(12) United States Patent
Jarrell et al.

(10) Patent No.: US 7,435,562 B2
(45) Date of Patent: Oct. 14, 2008

(54) MODULAR VECTOR SYSTEMS

(75) Inventors: Kevin A. Jarrell, Lincoln, MA (US);
William F. Donahue, Quincy, MA (US);
Brian M. Turczyk, Peabody, MA (US)

(73) Assignees: Modular Genetics, Inc., Cambridge, MA (US); The Trustees of Boston University, Boston, MA (US)

( * ) Notice: Subject to any disclaimer, the term of this patent is extended or adjusted under 35 U.S.C. 154(b) by 28 days.

(21) Appl. No.: 10/383,135

(22) Filed: Mar. 5, 2003

(65) Prior Publication Data

US 2004/0161752 A1 Aug. 19, 2004

(51) Int. Cl.
*C12P 19/34* (2006.01)
*C07H 21/04* (2006.01)
(52) U.S. Cl. .................... 435/91.5; 536/23.1
(58) Field of Classification Search ............... 435/91.2
See application file for complete search history.

(56) References Cited

U.S. PATENT DOCUMENTS

| | | | |
|---|---|---|---|
| 5,498,531 A | 3/1996 | Jarrell | 435/91.31 |
| 5,580,723 A | 12/1996 | Wells et al. | 435/6 |
| 5,780,272 A | 7/1998 | Jarrell | 435/91.31 |
| 5,834,250 A | 11/1998 | Wells et al. | 435/7.1 |
| 6,013,478 A | 1/2000 | Wells et al. | 435/69.1 |
| 6,171,820 B1 | 1/2001 | Short | 435/69.1 |
| 6,277,632 B1 | 8/2001 | Harney | 435/320.1 |
| 6,495,318 B2 | 12/2002 | Harney | 435/6 |
| 6,537,776 B1 | 3/2003 | Short | 435/69.1 |
| 6,579,678 B1 | 6/2003 | Patten et al. | 435/6 |
| 6,605,449 B1 | 8/2003 | Short | 435/69.1 |
| 6,613,514 B2 | 9/2003 | Patten et al. | 435/6 |
| 6,794,142 B2* | 9/2004 | Laird et al. | 435/6 |
| 6,939,689 B2 | 9/2005 | Short et al. | 435/69.1 |
| 6,946,296 B2 | 9/2005 | Patten et al. | 435/440 |
| 6,972,183 B1 | 12/2005 | Lafferty et al. | 435/7.4 |
| 6,979,733 B2 | 12/2005 | Zhao et al. | 536/23.2 |
| 6,995,017 B1 | 2/2006 | Stemmer | 435/440 |
| 7,018,793 B1 | 3/2006 | Short | 435/6 |
| 7,024,312 B1 | 4/2006 | Selifonov et al. | 702/19 |
| 7,078,035 B2 | 7/2006 | Short et al. | |
| 7,078,504 B2 | 7/2006 | Short et al. | |
| 7,105,297 B2 | 9/2006 | Minshull et al. | |
| 7,148,054 B2 | 12/2006 | Del Cardayre et al. | |
| 7,232,672 B2 | 6/2007 | Weiner et al. | 435/189 |
| 7,232,677 B2 | 6/2007 | Short et al. | 435/196 |
| 7,314,613 B2 | 1/2008 | Patten et al. | |
| 7,318,918 B2 | 1/2008 | Patten et al. | |
| 2005/0129059 A1 | 6/2005 | Jiang et al. | |
| 2005/0186622 A1 | 8/2005 | Stemmer et al. | |
| 2005/0191688 A1 | 9/2005 | Selifonov et al. | |
| 2005/0266465 A1 | 12/2005 | Williams et al. | |
| 2006/0008844 A1 | 1/2006 | Stemmer et al. | |
| 2006/0045888 A1 | 3/2006 | Punnonen et al. | |
| 2006/0047611 A1 | 3/2006 | Selifonov et al. | |
| 2006/0051795 A1 | 3/2006 | Crameri et al. | |
| 2006/0084091 A1 | 4/2006 | Patten et al. | |
| 2006/0166225 A1 | 7/2006 | Patten et al. | |
| 2006/0177831 A1 | 8/2006 | Stemmer et al. | |
| 2006/0205003 A1 | 9/2006 | Gustafsson et al. | |
| 2006/0223143 A1 | 10/2006 | Patten et al. | |
| 2006/0234299 A1 | 10/2006 | Stemmer et al. | |
| 2006/0257890 A1 | 11/2006 | Minshull et al. | |
| 2006/0259995 A1 | 11/2006 | Cayouette et al. | |
| 2006/0275804 A1 | 12/2006 | Short et al. | |
| 2006/0286603 A1 | 12/2006 | Kolkman et al. | |
| 2007/0020235 A1 | 1/2007 | Patten et al. | |
| 2007/0020734 A1 | 1/2007 | Patten et al. | |
| 2007/0025966 A1 | 2/2007 | Patten et al. | |
| 2007/0026446 A1 | 2/2007 | del Cardayre et al. | |
| 2007/0031878 A1 | 2/2007 | Patten et al. | |
| 2007/0031943 A1 | 2/2007 | Jarrell et al. | |
| 2007/0048775 A1 | 3/2007 | Cardayre et al. | |
| 2007/0054313 A1 | 3/2007 | Crameri et al. | |
| 2007/0056053 A1 | 3/2007 | Gray et al. | |
| 2007/0065407 A1 | 3/2007 | Patten et al. | |
| 2007/0065838 A1 | 3/2007 | Crameri et al. | |
| 2007/0087373 A1 | 4/2007 | Punnonen et al. | |
| 2007/0087374 A1 | 4/2007 | Punnonen et al. | |
| 2007/0092887 A1 | 4/2007 | Stemmer et al. | |
| 2007/0274950 A1 | 11/2007 | Patten et al. | |
| 2007/0292954 A1 | 12/2007 | Elledge | |
| 2008/0031853 A1 | 2/2008 | Patten et al. | |
| 2008/0032378 A1 | 2/2008 | Callen et al. | |
| 2008/0047037 A1 | 2/2008 | Callen et al. | |
| 2008/0076710 A1 | 3/2008 | Patten et al. | |

FOREIGN PATENT DOCUMENTS

EP  01528067  5/2005

(Continued)

OTHER PUBLICATIONS

Stump et al., Nucl. Acids Res., 27 (23), 4642-4648, 1999.*
Coljee et al., Nature Biotechnology, vol. 18, 789-791, 2000.*
Gade, et al., "Incorporation of Nonbase Residues into Synthetic Oligonucleotides and Their Use in the PCR", *GATA*, 10(2): 61-65, 1993.
Newton, et al., "The Production of PCR Products with 5' Single-Stranded Tails Using Primers that Incorporate Novel Phosphoramidite Intermediates", *Nucleic Acids Research*, 21(5): 1155-1162, 1993.

(Continued)

*Primary Examiner*—Nancy Vogel
(74) *Attorney, Agent, or Firm*—Margo H. Furman; Brenda Herschbach Jarrell; Choate, Hall & Stewart LLP

(57) ABSTRACT

The present invention provides improved techniques and reagents for producing nucleic acid molecules. In certain preferred embodiments, the nucleic acid molecules are modular vectors. In certain preferred embodiments, the nucleic acid molecules are produced in polymerase chain reactions employing terminator primer residues.

15 Claims, 14 Drawing Sheets

FOREIGN PATENT DOCUMENTS

| | | |
|---|---|---|
| EP | 01555316 | 7/2005 |
| EP | 1565 205 | 8/2005 |
| EP | 1576 108 | 9/2005 |
| EP | 1201 768 | 12/2005 |
| EP | 01108058 | 2/2006 |
| EP | 01690868 A1 | 8/2006 |
| EP | 01696025 A2 | 8/2006 |
| EP | 01696025 A3 | 9/2006 |
| EP | 01707641 A2 | 10/2006 |
| EP | 0839185 B1 | 11/2006 |
| EP | 01717322 A2 | 11/2006 |
| EP | 01707641 A3 | 12/2006 |
| EP | 01717322 | 1/2007 |
| JP | 2005/245453 | 9/2005 |
| JP | 2007244399 | 9/2007 |
| JP | 2007252382 | 10/2007 |
| WO | EP01644394 | 3/2005 |
| WO | WO 2005/093099 | 10/2005 |
| WO | WO 2005/093101 | 10/2005 |
| WO | WO 2005/097992 | 10/2005 |
| WO | 2005113592 | 12/2005 |
| WO | WO 2005/113592 | 12/2005 |
| WO | WO 2005/118853 | 12/2005 |
| WO | WO 2006/009888 | 1/2006 |
| WO | WO-06/028684 A2 | 3/2006 |
| WO | WO 2006/028684 | 3/2006 |
| WO | WO-06/083276 A2 | 8/2006 |
| WO | WO-06/096527 A2 | 9/2006 |
| WO | WO-06/099207 A2 | 9/2006 |
| WO | WO-06/101584 A2 | 9/2006 |
| WO | WO-06/127040 A2 | 11/2006 |
| WO | WO 2007/044083 | 4/2007 |
| WO | WO-2007/044083 | 4/2007 |
| WO | WO-2007/124065 | 11/2007 |

OTHER PUBLICATIONS

Bolivar, et al., "Construction and Characterization of New Cloning Vehicles", II. A Multipurpose Cloning System *Gene*, 2:95-113, 1977.
Chang, et al., "Construction and Characterization of Amplifiable Multicopy DNA Cloning Vehicles Derived from the P15A Cryptic Miniplasmid"; *J. Bacteriol.* 134: 1141-1156, 1978.
Fukushige, et al., "Genomic Targeting with a Positive-Selection *lox* Integration Vector Allows Highly Reproducible Gene Expression in Mammalian Cells", *Proc. Natl. Acad. Sci. USA*, 7905-7909, 1992.
Jackson, et al., "Biochemical Method for Inserting New Genetic Information in DNA of Simian Virus 40: Circular SV40 DNA Molecules Containing Lambda Phage Genes and the Galactose Operon of *Escherichia coli*", *Proc. Natl. Acad. Sci. USA*, 69: 2904-2909, 1972.
Kahn, et al., "Plasmid Cloning Vehicles Derived from Plasmids ColE1, F, R6K, and RK2", *Method. Enzymol.* 68: 268-280, 1979.
Stocker, et al., "Versatile Low-Copy-Number Plasmid Vectors for Cloning in *Escherichia coli*", *Gene*, 18: 335-341, 1982.
Uhlin, et al., "New Runaway-Replication-Plasmid Cloning Vectors and Suppression of Runaway Replication by Novobiocin", *Gene*, 22: 225-265, 1983.
Doyle, "High-throughput Cloning For Proteomics Research," *Methods Mol. Biol.*, 310: 107-113, 2005.
Li, et al., "Ligation Independent Cloning Irrespective Of Restriction Site Compatibility," *Nucl. Acids Res.*, 25(20): 4165-4166, 1997.
Nisson, "Rapid and Efficient Cloning Of Alu-PCR Products Using Uracil DNA Glycosylase," *PCR Methods Appl.*, 1(2): 120-123, 1991.
Patten, et al., "Applications Of DNA Shuffling To Pharmaceuticals And Vaccines," *Curr Opin Biotechnol.*, 8(6): 724-733, 1997.

Silverman, et al., "Multivalent Avimer Proteins Evolved By Exon Shuffling Of A Family Of Human Receptor Domains," *Nature Biotech.*, 23: 1556-1561, 2005.
Abelian, A., et al., "Targeting The A Site RNA Of The *Escherichia coli* Ribosomal 30 S Subunit By 2'-O-Methyl Oligoribonucleotides: A Quantitative Equilibrium Dialysis Binding Assay And Differential Effects Of Aminoglycoside Antibiotics.", *Biochem. Journal* 383(2):201-208, 2004.
Kierzek, E., et al., "The Influence Of Locked Nucleic Acid Residues On The Thermodynamic Properties Of 2'-O-Methyl RNA/RNA Heteroduplexes.", *Nucleic Acid Research* 33(16): 5082-5093, 2005.
Sandbrink, J., et al., "Investigation Of Potential RNA Bulge Stabilizing Elements.", *J Mol Recognit* 18(4): 318-326, 2005.
Suzuki, Y., et al., "A Novel High-Throughput (HTP) Cloning Strategy For Site-Directed Designed Chimeragenesis And Mutation Using The Gateway Cloning System.", *Nucleic Acid Research* 33(12): e109 (1-6), 2005.
Wright, A., et al., "Diverse Plasmid DNA Vectors By Directed Molecular Evolution Of Cytomegalovirus Promoters.", *Human Gene Therapy* 16(7): 881-892, 2005.
Demarest et al., "Engineering stability into *Escherichia coli* secreted Fabs leads to increased functional expression", *Protein Eng Des Sel*, 19(7): 325-36, 2006.
Li, et al., *Applied Microbio. And Biotech.*, 75(3): 703-709, 2007.
Li, et al., *Nature Methods YNat. Methods*, 4(3): 251-256, 2007.
Zhu, *Biotechniques*, 43: 356-359, 2007.
Ailenberg, et al., "Description of a PCR-based technique for DNA splicing and mutagenesis by producing 5' overhangs with run through stop DNA synthesis utilizing Ara-C", BMC Biotechnology, Biomed Central LTD., 5(1):23-28, 2005.
Ailenberg, et al., "Site-directed mutagenesis using a PCR-based staggered re-annealing method without restriction enzymes", Biotechniques, 22(4):624-630, 1997.
Coljee, et al., "Seamless gene engineering using RNA- and DNA-overhang cloning", Nature Biotechnology, 18:789-791, 2000.
Donahue, et al., "Rapid gene cloning using terminator primers and modular vectors", Nucleic Acids research, 30(18):E95, 2002.
Barnes, *PNAS*, 91:2216-2220, 1994.
Bolivar, et al., *Gene*, 2: 75-93, 1977.
Cadwell, et al., *PCR Methods Appl.*, 2: 28-33, 1992.
Chen et al., *J. Am. Chem. Soc.*, 11: 8799-8800, 1994.
Crameri, et al., *BioTechniques*, 18: 194-196, 1995.
Dillon, et al., *BioTechniques*, 9:298-300, 1990.
Goeddel, et al., *PNAS*, 76: 106-110, 1979.
Hayashi, et al., *BioTechniques*, 17: 310-314, 1994.
Heyneker, et al., *Nature*, 263: 748-752, 1976.
Hermes, et al., *Gene*, 84: 143-151, 1989.
Itakura, et al., *Science*, 198: 1056-1063, 1977.
Lashkari, et al., *PNAS*, 92: 7912-7915, 1995.
Mandecki, et al., *Gene*, 68: 101-107, 1988.
Mandecki, et al., *Gene*, 94: 103-107, 1992.
Prodromou, et al., *Protein Eng.*, 5: 827-829, 1992.
Stemmer, *Nature*, 370: 389-391, 1994.
Stemmer, *PNAS*, 91: 10747-10751, 1994.
Watson, *Gene*, 70: 399-403, 1988.
Stemmer et al., "Single-step assembly of a gene and entrier plasmid from large numbers of oligodeoxyribonucleotides", Gene, 164: 49-53, 1995.
Li et al., "Harnessing homologous recombination in vitro to generate recombinant DNA via SLIC", Nature Methods, 4(3): 251-56, 2007.
Wu et al., "Simplified gene synthesis: A one-step approach to PCR-base gene construction", Journal of Biotechnology, 124: 496-506, 2006.
Kodumal et al., "Total synthesis of long DNA sequences: Synthesis of a contiguous 32-kb polyketide synthase gene cluster", PNAS, 101(44): 15573-78, 2004.

\* cited by examiner

1) Ligate Insert
2) Helper phage will circularize /Excise
3) White colonies should contain Insert

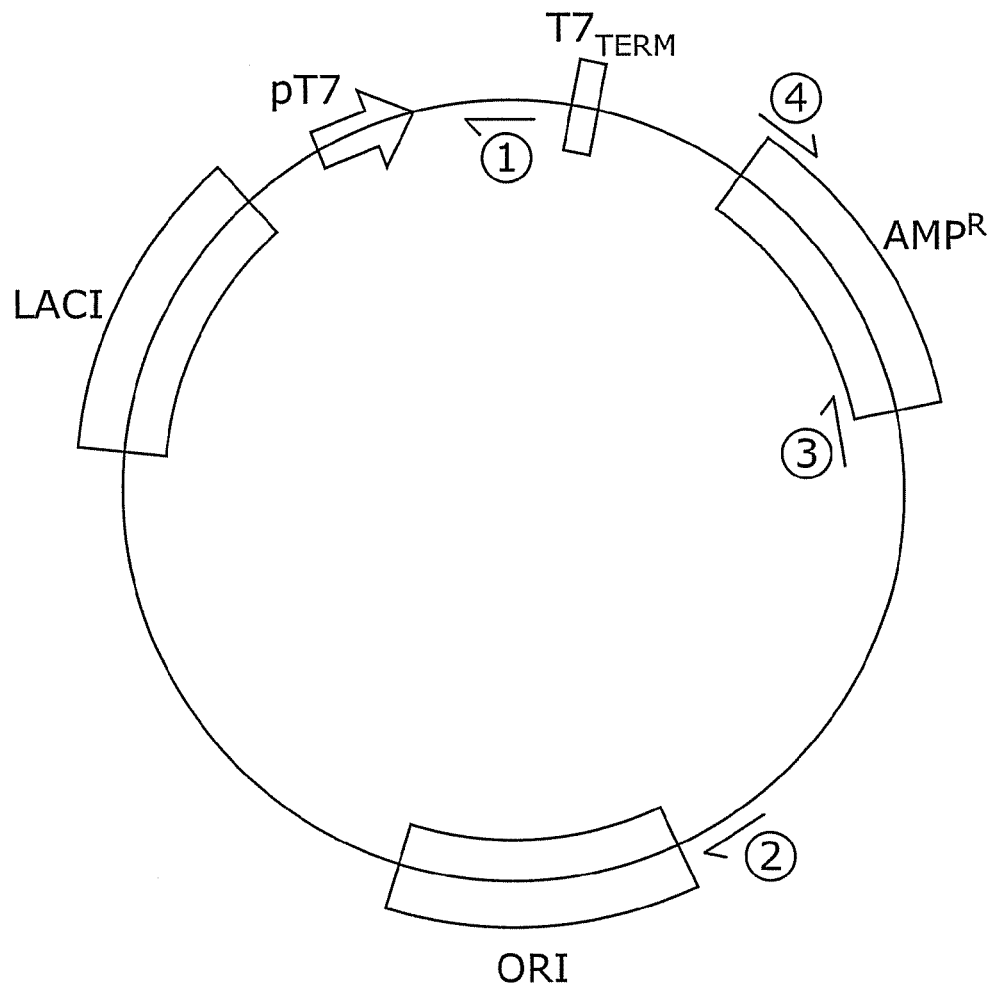
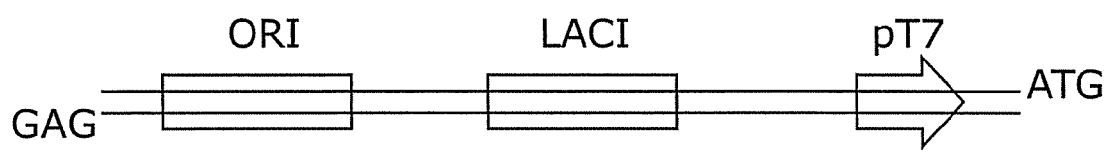
FIG. 9A

3nt + 1nt Ribo Terminator Cloning
(2 molecule Vector)

(A)

| ORI | 2400 nt | - size

[3nt] - 5'OST - CTG CTA AGT GAG cuc GAC AGA TCG CTG AGA TAG GTG C   *(RNA: cuc)*

[3nt] - 3'OHT - AAG CTT GCT AGG uag GCT ACG TCT TGC TGG CGT TCG   *(RNA: uag)*

| KAN | 1267 | - size

[3nt] - 5'KHT - CTA CCT AGC AAG cuu CTA TCT GGA CAA GGG AAA ACG   *(RNA: cuu)*

[3nt] - 3'KST - GAG CTC ACT TAG cag GGC GAA AAC TCT CAA GGA TC   *(RNA: cag)*

(B)

| ORI (s) | 824 | - size

[1nt] - 1NT5'ORI - TTG CTA AGT GAG CTc GAC AGA TCG CTG AGA TAG GTG C   *(RNA: c)*

- 1NT3'ORI (s) - AAG CTT GCT AGG TAg GGC GTT TTT CCA TAG GCT CCG   *(RNA: g)*

| KAN | 1267 | - size

[1nt] - 1NT5'KAN - CTA CCT AGC AAG CTu CTA TCT GGA CAA GGG AAA ACG   *(RNA: u)*

- 1NT3'KAN - GAG CTC ACT TAG CAa GGC GAA AAC TCT CAA GGA   *(RNA: a)*

FIG. 11

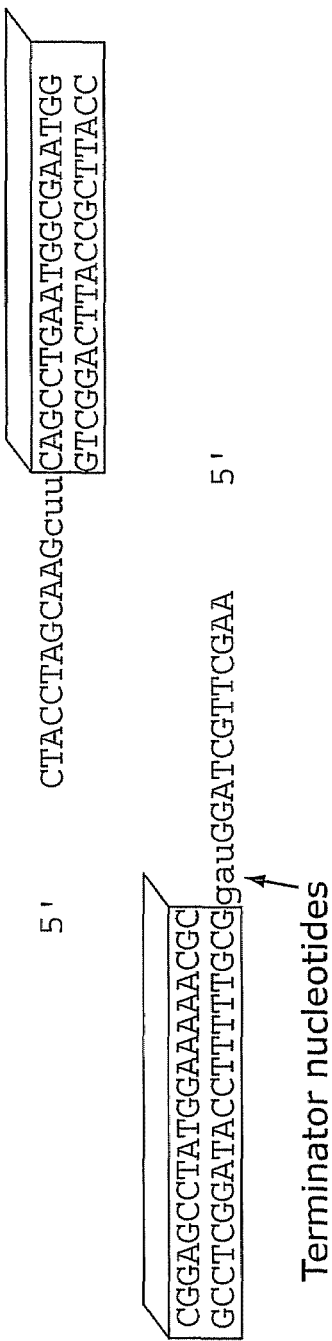
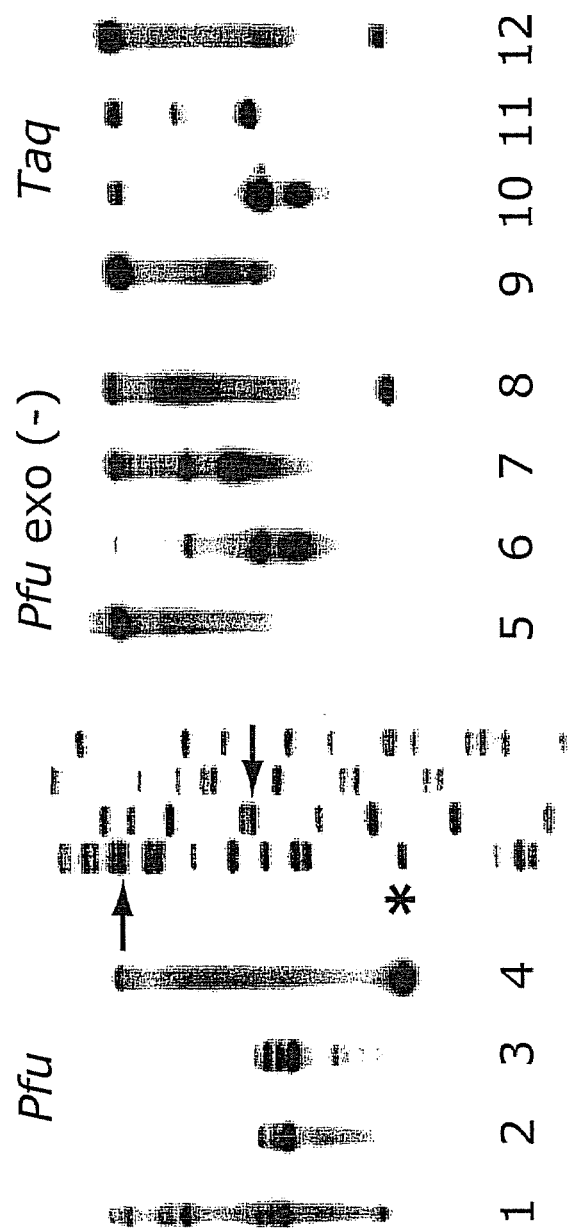
FIG. 13A
FIG. 13B

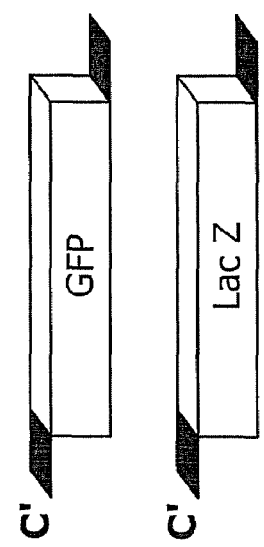
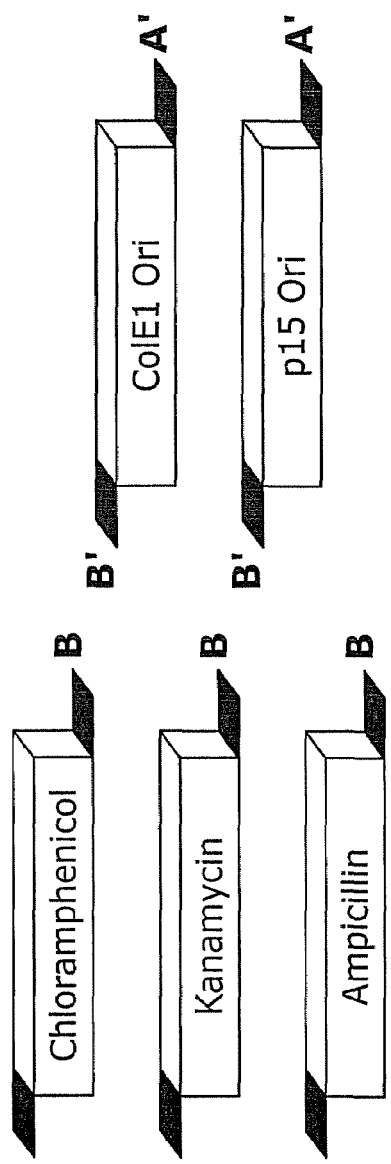
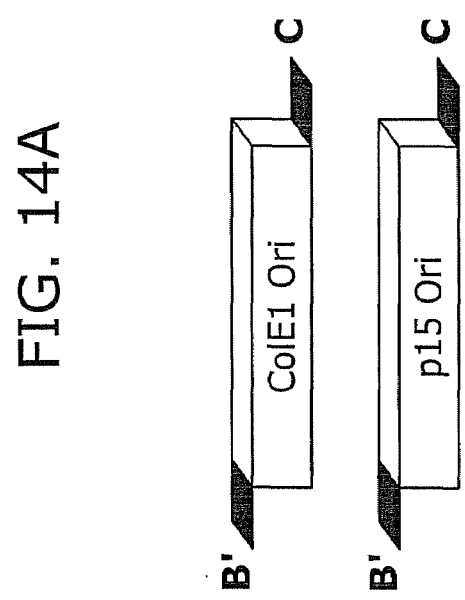
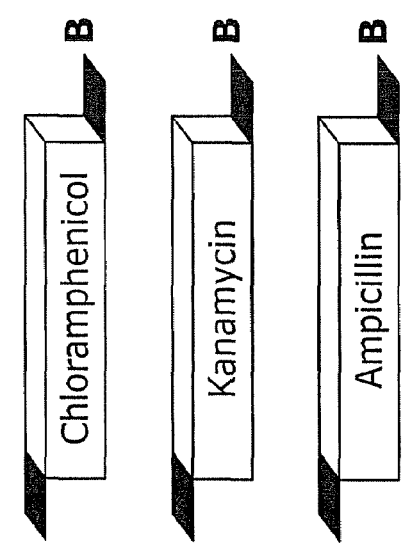
FIG. 14A
FIG. 14B

Lanes 1, 5, 9 - Single ribonucleotide
Lanes 2, 6, 10 - Single 2'-O-methyl ribonucleotide
Lanes 3, 7, 11 - Three ribonucleotide
Lanes 4, 8, 12 - DNA oligonucleotide

SEQUENCE LISTING

<160> NUMBER OF SEQ ID NOS: 43

<210> SEQ ID NO 1
<211> LENGTH: 23
<212> TYPE: DNA
<213> ORGANISM: Artificial Sequence
<220> FEATURE:
<223> OTHER INFORMATION: Description of Combined DNA/RNA Molecule:Vector
      Fragments
<220> FEATURE:
<223> OTHER INFORMATION: Description of Artificial Sequence: PCR primer,
      used for cloning.

<400> SEQUENCE: 1
cauggtatat ctccttctta aag                                              23

<210> SEQ ID NO 2
<211> LENGTH: 22
<212> TYPE: DNA
<213> ORGANISM: Artificial Sequence
<220> FEATURE:
<223> OTHER INFORMATION: Description of Combined DNA/RNA Molecule:Vector
      Fragments.
<220> FEATURE:
<223> OTHER INFORMATION: Description of Artificial Sequence:PCR primer,
      used for cloning.

<400> SEQUENCE: 2
cucatgacca aaatcccuta ac                                               22

<210> SEQ ID NO 3
<211> LENGTH: 22
<212> TYPE: DNA
<213> ORGANISM: Artificial Sequence
<220> FEATURE:
<223> OTHER INFORMATION: Description of Combined DNA/RNA Molecule:Vector
      Fragments.
<220> FEATURE:
<223> OTHER INFORMATION: Description of Artificial Sequence: PCR primer,
      used for cloning.

<400> SEQUENCE: 3
gagattatca aaaggatct tc                                                22

<210> SEQ ID NO 4
<211> LENGTH: 20
<212> TYPE: DNA
<213> ORGANISM: Artificial Sequence
<220> FEATURE:
<223> OTHER INFORMATION: Description of Combined DNA/RNA Molecule:Vector
      Fragments.
<220> FEATURE:
<223> OTHER INFORMATION: Description of Artificial Sequence: PCR primer,
      used for cloning.

<400> SEQUENCE: 4
uaactagcat aaccccttgg                                                  20

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:Insert
      Fragments.
<220> FEATURE:
<223> OTHER INFORMATION: Description of Artificial Sequence: PCR primer,
      used for cloning.

```
<400> SEQUENCE: 5
augaccauga uuacgccaac g                                              21

<210> SEQ ID NO 6
<211> LENGTH: 22
<212> TYPE: DNA
<213> ORGANISM: Artificial Sequence
<220> FEATURE:
<223> OTHER INFORMATION: Description of Combined DNA/RNA Molecule:Insert
      Fragment.
<220> FEATURE:
<223> OTHER INFORMATION: Description of Artificial Sequence: PCR primer,
      used for cloning.

<400> SEQUENCE: 6
uuacaauuuc cauucgccau uc                                             22

<210> SEQ ID NO 7
<211> LENGTH: 36
<212> TYPE: DNA
<213> ORGANISM: Artificial Sequence
<220> FEATURE:
<223> OTHER INFORMATION: Description of Combined DNA/RNA Molecule:Vector
      Fragment.
<220> FEATURE:
<223> OTHER INFORMATION: Description of Artificial Sequence: PCR primer,
      used for cloning.

<400> SEQUENCE: 7
ctacctagca agcuucuauc uggacaaggg aaaacg                              36

<210> SEQ ID NO 8
<211> LENGTH: 41
<212> TYPE: DNA
<213> ORGANISM: Artificial Sequence
<220> FEATURE:
<223> OTHER INFORMATION: Description of Combined DNA/RNA Molecule:Vector
      Fragments.
<220> FEATURE:
<223> OTHER INFORMATION: Description of Artificial Sequence:PCR primer,
      used for cloning.

<400> SEQUENCE: 8
ccctatagtg agtcgtatta aggcgaaaac tctcaaggat c                        41

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 9
ttaatacgac tcactatagg gatggaagac gccaaaaaca ta                       42

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 10
gagctcactt agcagttaca atttggactt tccgcc                              36
```

<210> SEQ ID NO 11
<211> LENGTH: 36
<212> TYPE: DNA
<213> ORGANISM: Artificial Sequence
<220> FEATURE:
<223> OTHER INFORMATION: Description of Combined DNA/RNA
      Molecule:Ribonucleotides.
<220> FEATURE:
<223> OTHER INFORMATION: Description of Artificial Sequence:PCR primer,
      used for cloning.

<400> SEQUENCE: 11
ctacctagca agctuctatc tggacaaggg aaaacg                                36

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence:PCR primer,
      used for cloning.

<400> SEQUENCE: 12
gagctcactt agcaaggcga aaactctcaa gga                                   33

<210> SEQ ID NO 13
<211> LENGTH: 37
<212> TYPE: DNA
<213> ORGANISM: Artificial Sequence
<220> FEATURE:
<223> OTHER INFORMATION: Description of Combined DNA/RNA
      Molecule:Ribonucleotides.
<220> FEATURE:
<223> OTHER INFORMATION: Description of Artificial Sequence: PCR primer,
      used for cloning.

<400> SEQUENCE: 13
ttgctaagtg agcucgacag atcgctgaga taggtgc                               37

<210> SEQ ID NO 14
<211> LENGTH: 36
<212> TYPE: DNA
<213> ORGANISM: Artificial Sequence
<220> FEATURE:
<223> OTHER INFORMATION: Description of Combined DNA/RNA Molecule:Kan
      Fragment.
<220> FEATURE:
<223> OTHER INFORMATION: Description of Artificial Sequence: PCR primer,
      used for cloning.

<400> SEQUENCE: 14
aagcttgcta agtagggcgt ttttccatag gctccg                                36

<210> SEQ ID NO 15
<211> LENGTH: 36
<212> TYPE: DNA
<213> ORGANISM: Artificial Sequence
<220> FEATURE:
<223> OTHER INFORMATION: Description of Combined DNA/RNA
      Molecule:Kanamycin.
<220> FEATURE:
<223> OTHER INFORMATION: Description of Artificial Sequence:PCR primer,
      used for cloning.

<400> SEQUENCE: 15
ctacctagca agctuctatc tggacaaggg aaaacg                                36

<210> SEQ ID NO 16

```
<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence:PCR primer,
      used for cloning.

<400> SEQUENCE: 16
gagctcactt agcaaggcga aaactctcaa ggatc                              35

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:PCR primer,
      used for cloning.

<400> SEQUENCE: 17
ctagacagtt cagtcctatc tggacaaggg aaaacg                             36

<210> SEQ ID NO 18
<211> LENGTH: 34
<212> TYPE: DNA
<213> ORGANISM: Artificial Sequence
<220> FEATURE:
<223> OTHER INFORMATION: Description of Combined DNA/RNA
      Molecule:Ampicillin.
<220> FEATURE:
<223> OTHER INFORMATION: Description of Artificial Sequence:PCR primer,
      used for cloning.

<400> SEQUENCE: 18
ctacctagca agctucagcc tgaatggcga atgg                               34

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 19
gagctcactt agcaaggtca tgagattatc aaaaagg                            37

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 20
ctagacagtt cagtccagcc tgaatggcga atgg                               34

<210> SEQ ID NO 21
<211> LENGTH: 36
<212> TYPE: DNA
<213> ORGANISM: Artificial Sequence
<220> FEATURE:
<223> OTHER INFORMATION: Description of Combined DNA/RNA
      Molecule:Chloramphenicol.
<220> FEATURE:
<223> OTHER INFORMATION: Description of Artificial Sequence: PCR primer,
      used for cloning.

<400> SEQUENCE: 21
```
ctacctagca agctuccgaa taaatacctg tgacgg 36

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 22
gagctcactt agcaagcctc aggcatttga gaagc 35

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 23
ctagacagtt cagtcccgaa taaatacctg tgacgg 36

<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 24
gactgaactg tctagaatgc agctggcacg acag 34

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 25
gatgacttga cagacgatta gggtgatggt tcacg 35

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 26
gactgaactg tctagagcgc aacgcaatta atgtg 35

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 27
gatgacttga cagacgatta gggtgatggt tcacg            35

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 28
ttgctaagtg agctcatccc ttaacgtgag ttttcg           36

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 29
aagcttgcta ggtaggaggc ggtttgcgta ttgg             34

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 30
gtctgtcaag tcatcgaggc ggtttgcgta ttgg             34

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 31
ttgctaagtg agctcctacc gcattaaagc ttatcg           36

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 32
aagcttgcta ggtaggcgtc gggtgatgct gcc              33

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 33
gtctgtcaag tcatcgcgtc gggtgatgct gcc              33

<210> SEQ ID NO 34
<211> LENGTH: 37
<212> TYPE: DNA
<213> ORGANISM: Artificial Sequence
<220> FEATURE:
<223> OTHER INFORMATION: Description of Combined DNA/RNA Molecule:Vector Primer.
<220> FEATURE:
<223> OTHER INFORMATION: Description of Artificial Sequence:PCR primer, used for cloning.

<400> SEQUENCE: 34
ctgctaagtg agcucgacag atcgctgaga taggtgc     37

<210> SEQ ID NO 35
<211> LENGTH: 36
<212> TYPE: DNA
<213> ORGANISM: Artificial Sequence
<220> FEATURE:
<223> OTHER INFORMATION: Description of Combined DNA/RNA Molecule:Vector Primer.
<220> FEATURE:
<223> OTHER INFORMATION: Description of Artificial Sequence: PCR primer, used for cloning.

<400> SEQUENCE: 35
aagcttgcta gguaggctac gtcttgctgg cgttcg     36

<210> SEQ ID NO 36
<211> LENGTH: 36
<212> TYPE: DNA
<213> ORGANISM: Artificial Sequence
<220> FEATURE:
<223> OTHER INFORMATION: Description of Combined DNA/RNA Molecule:Vector Primer.
<220> FEATURE:
<223> OTHER INFORMATION: Description of Artificial Sequence: PCR primer, used for cloning.

<400> SEQUENCE: 36
ctacctagca agcuuctatc tggacaaggg aaaacg     36

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: PCR primer, used for cloning.

<400> SEQUENCE: 37
gagctcactt agcaaggcga aaactctcaa gga     33

<210> SEQ ID NO 38
<211> LENGTH: 53
<212> TYPE: DNA
<213> ORGANISM: Artificial Sequence
<220> FEATURE:
<223> OTHER INFORMATION: Description of Combined DNA/RNA Molecule:Terminator Nucleotides.
<220> FEATURE:
<223> OTHER INFORMATION: Description of Artificial Sequence: PCR primer, used for cloning.

<400> SEQUENCE: 38
ctacctagca agcuucagcc tgaatggcga atgggtcgga cttaccgctt acc     53

```
<210> SEQ ID NO 39
<211> LENGTH: 55
<212> TYPE: DNA
<213> ORGANISM: Artificial Sequence
<220> FEATURE:
<223> OTHER INFORMATION: Description of Combined DNA/RNA
      Molecule:Terminator Nucleotides.
<220> FEATURE:
<223> OTHER INFORMATION: Description of Artificial Sequence: PCR primer,
      used for cloning.

<400> SEQUENCE: 39
cggagcctat ggaaaaacgc gcctcggata ccttttttgcg gauggatcgt tcgaa         55

<210> SEQ ID NO 40
<211> LENGTH: 53
<212> TYPE: DNA
<213> ORGANISM: Artificial Sequence
<220> FEATURE:
<223> OTHER INFORMATION: Description of Combined DNA/RNA Molecule:Three
      Ribonucleotides.
<220> FEATURE:
<223> OTHER INFORMATION: Description of Artificial Sequence: PCR primer,
      used for cloning.

<400> SEQUENCE: 40
ctacctagca agcucagcc tgaatggcga atgggtcgga cttaccgctt acc             53

<210> SEQ ID NO 41
<211> LENGTH: 55
<212> TYPE: DNA
<213> ORGANISM: Artificial Sequence
<220> FEATURE:
<223> OTHER INFORMATION: Description of Artificial Sequence: PCR primer,
      used for cloning.

<400> SEQUENCE: 41
cggagcctat ggaaaaacgc gcctcggata ccttttttgcg gatggatcgt tcgaa         55

<210> SEQ ID NO 42
<211> LENGTH: 37
<212> TYPE: DNA
<213> ORGANISM: Artificial Sequence
<220> FEATURE:
<223> OTHER INFORMATION: Description of Combined DNA/RNA Molecule:Insert
      fragment.
<220> FEATURE:
<223> OTHER INFORMATION: Description of Artificial Sequence:PCR primer,
      used for cloning.

<400> SEQUENCE: 42
ctgctaagtg agcucgacag atcgctgaga taggtgc                              37

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence:PCR primer,
      used for cloning.

<400> SEQUENCE: 43
aagcttgcta agtagggcgt ttttccatag gctccg                               36
```

MODULAR VECTOR SYSTEMS

GOVERNMENT FUNDING

Some or all of the work described herein was supported by grant number MCB9604458 from the National Science Foundation and/or grant number AI48665 from the National Institutes of Health; the Unites States Government may have certain rights in the invention.

PRIORITY CLAIM AND RELATED APPLICATIONS

The present application claims priority under 35 USC § 119 to U.S. Ser. No. 60/362,253, filed Mar. 6, 2002, the entire contents of which are incorporated herein by reference. The present application is also related to co-pending applications U.S. Ser. No. 09/225,990, filed Jan. 5, 1999, U.S. Ser. No. 09/897,712, filed Jun. 29, 2001 (a nationalized application corresponding to PCT/US00/00189, filed Jan. 5, 2000), U.S. Ser. No. 09/910,354, filed Jul. 20, 2001, and also to U.S. Ser. No. 60/219,820, filed Jul. 21, 2000; the entire contents of each of these applications are incorporated herein by reference.

BACKGROUND OF THE INVENTION

Perhaps the classic genetic manipulation in molecular biology is the cleavage of a circular vector with one or more restriction enzymes and the ligation of a selected insert into the linearized vector. Since the 1970s, when the pioneers of molecular biology first demonstrated such manipulation to be feasible, significant research effort has been invested in the development of improved vector systems (see discussion of vectors derived from plasmids in Ausubel et al., *Current Protocols in Molecular Biology*, Section II, 1.5.1-1.5.17, John Wiley & Sons, 1998, incorporated herein by reference).

To give but a few examples, plasmid vectors that replicate in different hosts, with different copy numbers, have been prepared (e.g., bacterial vectors designed to have either relaxed or stringent control of replication; yeast vectors with either a 2µ or centromeric replication origin, mammalian vectors containing viral [e.g., SV40 or BPV] origins of replication, etc.). Vectors have been engineered to allow ready detection of insertion events (e.g., by creation or disruption of a selectable or detectable marker), to direct high levels of expression of proteins encoded by inserted sequences (e.g., under the control of transcription, splicing, and/or translation signals active in a given host system), to generate gene fusions that allow analysis of expression of inserted sequences (e.g., by analysis of β-galactosidase, chloramphenicol transferase, luciferase, or green fluorescent protein activity, etc.), or to create fusion proteins with experimentally useful attributes (e.g., easy purification, desired cellular localization, etc.). Vectors have been designed that are particularly useful for determining the sequence of inserted fragments (e.g., by allowing easy production of single-stranded DNA), or for producing RNA (sense or antisense) from the inserted sequences. Most companies that sell molecular biology reagents include among their products vectors that they have developed to be particularly useful for designated applications (see, for example, catalogs provided by Amersham Pharmacia Biotech, Piscataway, N.J.; Promega Corporation, Madison, Wis.; Invitrogen Inc., Carlsbad, Calif.; Life Technologies, Inc., Rockville, Md.; New England Biolabs, Beverly, Mass.; Stratagene, Inc., La Jolla, Calif.).

Of course, the universe of genetic "vectors" is not limited to circular molecules derived from bacterial plasmids. Any nucleic acid molecule that includes sequences sufficient to direct in vivo or in vitro self-replication can be employed as a vector. Typically, such replication sequences include a replication origin that directs duplication of the vector sequence in a host system (typically a transformed cell). Alternatively, sequences that direct integration of the vector into another nucleic acid molecule that is present in and replicated by the relevant host system can be sufficient to achieve vector (and insert) replication.

Most vectors in use today are derived from naturally-occurring bacterial plasmids, bacteriophages, or other viruses. Some vectors contain features of more than one of these systems. Almost all of the commonly-used vectors contain one or more restriction sites designed for convenient insertion of fragments; most have at least one polylinker (see, for example, the vector database maintained at the URL vectorb-d.atcg.com/vectordb/vector.html, the contents of which as of Jul. 19, 2000 are included herein as Appendix A).

Despite the broad availability of vectors from commercial and other sources, each one has features selected by the relevant manufacturer rather than the experimental user. It is not uncommon for a researcher to have to modify an available vector to suit his experimental needs, or alternatively to modify his experimental design to accommodate the available vectors. There remains a need for the development of techniques and reagents that would allow a researcher to readily design and assemble vector(s) appropriate to his experimental needs.

SUMMARY OF THE INVENTION

The present invention encompasses the recognition that vectors are comprised of modular elements and need not be provided as discrete nucleic acid molecules into which fragments of interest are inserted. Rather, vectors can themselves be assembled from pieces that contain part or all of individual useful elements. In certain preferred embodiments of the invention, fragments corresponding to pieces of what is traditionally viewed as the "vector backbone" are provided individually and are linked to one another substantially simultaneously with the linkage that associates vector sequences with insert sequences.

According to the present invention, components of a vector can be defined as one of a variety of categories of vector elements. For example, sequences that allow the vector to replicate in a host system may be classified as "replication elements". Similarly, sequences that allow host cells containing a vector to survive experimental conditions that kill otherwise identical host cells lacking a vector may be classified as "replication elements"; sequences that allow detection but not selection of host cells containing vector sequences, or host cells containing vector and insert sequences, may be classified as "detectable elements"; sequences that can act to direct expression (i.e., transcription, splicing, and/or translation) of other sequences can be classified as "expression elements". Other categories of elements may also be defined as discussed in further detail herein.

The present invention allows a researcher to select individual elements from one or more categories of vector elements, and to combine the selected element(s) with one or more individual element(s) with one another to assemble vectors that contain a desired collection and arrangement of elements. Individual vector elements, or portions or combinations thereof, are provided on separate "vector fragments" that are linked together to create the final vector. Thus, the present invention provides techniques and reagents useful in the assembly of vectors from individual vector fragments.

Preferably, a vector assembled according to the present invention will include at least a replication element. More preferably, the vector will include one or more additional elements selected from the group consisting of additional replication elements (e.g., effective in different host systems), selectable markers, detectable markers, expression elements, fusion protein elements, mobile elements, recombination elements, cleavage site elements, etc. The inventive techniques and reagents may be employed to link two or more vector fragments to one another, serially or simultaneously, and also to link vector fragments with one or more insert fragments (again, serially or simultaneously).

In particularly preferred embodiments of the present invention, one or more of the vector and insert fragments used in the assembly of a final hybrid construct is prepared without the use of restriction enzymes (or any endonuclease). Most preferably, substantially all of the fragments that become linked together to produce a final assembled molecule are prepared without the use of restriction enzymes. In particularly preferred embodiments of the invention, RNA-Overhang Cloning and/or DNA Overhang Cloning are employed to produce vector and/or insert fragments. Also, in certain preferred embodiments of the invention, vector fragments, and optionally insert fragments, are linked to one another by ligation-independent cloning (i.e., without the use of a ligase enzyme).

DESCRIPTION OF THE DRAWING

FIG. 11 shows the primers used (3NT5'OST [SEQ ID NO:34]; 3NT3'OHT [SEQ ID NO:35]; 3NT5'KHT [SEQ ID NO:36]; 3NT3'KST [SEQ ID NO:37]; 1NT5'ORI [SEQ ID NO:13]; 1NT3'Ori(s) [SEQ ID NO:14]; 1NT5'KAN [SEQ ID NO:11]; 1NT3'KAN [SEQ ID NO:12]).

FIG. 13 shows that termination of polymerization generates double-stranded DNA with specific single-stranded tails. Panel A shows a diagram of PCR products with tails generated by termination of polymerization (CTACCTAG-CAAGcuuCAGCCTGAATGGCGAATGG [SEQ ID NO: 38], CCATTCGCCATTCAGGCTG [SEQ ID NO: 42], CGGAGCCTATGGAAAAACGC [SEQ ID NO: 39], AAGCTTGCTAGGuagGCGTTTTTCCATAGGCTCCG [SEQ ID NO: 43]). Deoxyribonucleotides are shown in upper case, ribonucleotides are shown in lover case. Panel B depicts the termination of polymerization by ribonucleotides and 2'-O-methyl nucleotides. PCR experiments were conducted with the following polymerases: Pfu (Lanes 1-4), Pfu exo- (lanes 5-8) and Taq (lanes 9-12). The same 32P-labeled primer was used as a PCR primer in each experiment. Four different unlabeled primers were used. The four primers were identical except for the inclusion of one or three ribonucleotides, or a single 2'-O-methyl nucleotide, at a particular position (see Panel A).

FIG. 14 shows components that were used in assembling modular vectors. The modules were produced by PCR amplification of vector elements using primers containing 2'-O-methyl residues at particular positions. Identical overhang sequences are used for modules of analogous function (e.g., drug resistance genes), which make the modules readily interchangeable. Panel A shows components used for combinatorial assembly of six vectors. Panel B shows components used for expression cloning of two different genes into each of six modular vectors.

Figure 1:
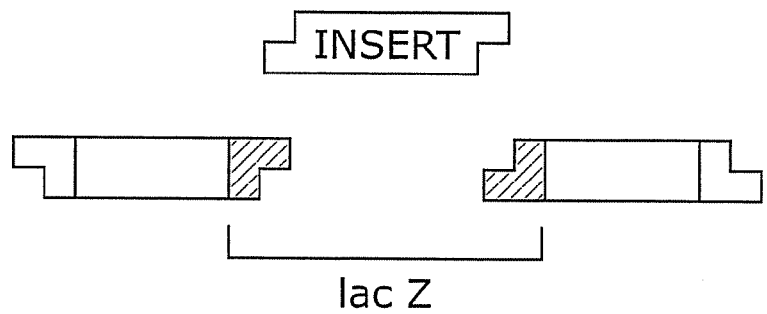
FIG. 1 depicts assembly of a hybrid molecule comprising λ vector elements and an insert, according to the present invention.

(CTACCTAGCAAGcuuCAGCCTGAATGGCGAATGG [SEQ ID NO:38],

CCATTCGCCATTCAGGCTG [SEQ ID NO:42],

CGGAGCCTATGGAAAAACGC [SEQ ID NO:39],

AGGCTTGCTAGGuagGCGTTTTTCCATAGGCTCCG [SEQ ID NO:43],

CTACCTAGCAAGCTuCAGCCTGAATGGCGAATGG) [SEQ ID NO:40],

CCATTCGCCATTCAGGCTG [SEQ ID NO:42],

CGGAGCCTATGGAAAAACGC [SEQ ID NO:41],

AAGCTTGCTAGGTAgGCGTTTTTCCATAGGCTCCG [SEQ ID NO:44]).

DEFINITIONS

"Element"—The term "element" is used herein to refer to a region of nucleic acid sequence that imparts a particular functional or structural characteristic upon the molecule.

"Expression"—"Expression" of a nucleic acid sequence, as that term is used herein, refers to one or more of the following events: (a) production of an RNA template from a DNA sequence (e.g., by transcription); (b) processing of an RNA transcript (e.g., by splicing, editing, and/or 3' end formation); (c) translation of an RNA has been into a polypeptide or protein; (d) post-translational modification of a polypeptide or protein.

"Fragment"—A "fragment", as that term is used herein, is an individual nucleic acid molecule that can be hybridized or linked with one or more other fragment molecules to produce a hybrid molecule. Preferably, a fragment contains at least a portion of a selected sequence element so that, when the fragments are linked together, a hybrid molecule is generated that contains a predetermined collection and arrangement of sequence elements. In certain preferred embodiments of the invention, each fragment contains at least one intact sequence element. In other preferred embodiments, each fragment contains only one intact sequence element. In still other preferred embodiments, at least one fragment contains only a portion of a particular sequence element (though the fragment may also contain a complete copy of a different sequence element). Preferably, that fragment will become linked with another fragment so that the complete sequence element is reassembled in the final hybrid. Alternatively or additionally, fragments are selected so that different hybrid molecules can be produced from linkage of the same collection of fragments, and such different hybrids can be distinguished from one another on the basis of whether a particular sequence element is recreated in the hybrid. Preferred fragments for use in accordance with the present invention are prepared without the use of restriction enzymes. Most preferably they are prepared by polymerase chain reaction (PCR) amplification according to ROC or DOC techniques (see, for example, U.S. Ser. Nos. 60/114,909, 09/225,990, and Coljee et al., *Nature Biotechnology* 18:789, July 2000, each of which is incorporated herein by reference in its entirety). Preferred fragments are double stranded nucleic acid molecules with at least one single-stranded overhang.

"Host system"—A "host system" according to the present invention is any in vivo or in vitro system into which a vector is introduced. Preferably, the host system is a cell or organism. Any type of cell, including a bacterial cell, yeast cell, plant cell, or animal cell, can be a host cell. Cells in culture and cells that are part of living tissues or organisms can also be host cells.

"Hybrid"—A "hybrid" nucleic acid molecule according to the present invention is a molecule produced by hybridization and/or linkage of at least two fragments or elements to one another.

"Linkage"—The "linkage" of two or more nucleic acid molecules to one another according to the present invention refers to any reaction that results in formation of a covalent bond between two nucleic acid molecules that were not covalently attached to one another prior to the linkage reaction. Preferably, the linkage is accomplished either by splicing or by ligation. Alternatively, linkage may be accomplished indirectly, for example by replication of molecule pairs (or clusters) held together by ligation but including one or more nicks. Linkage may occur in vitro or in vivo.

"Overhang"—An "overhang", according to the present invention, is a single-stranded region of nucleic acid extending from a double-stranded region. Preferred overhangs are at least one nucleotide long. Particularly preferred overhangs are at least 2, 3, 4, 5, 5, 6, 7, 8, 9, 10, 11, 12, 13, 14, 15, 20, or 25 nucleotides long. In some preferred embodiments of the invention, the overhangs are comprised of at least one, preferably at least 2, 3, 4, 5, or more RNA residues; in other preferred embodiments the overhangs are comprised of DNA. In some embodiments of the invention, overhangs may comprise RNA elements that include functional intronic sequences.

"Portion"—A "portion" of a nucleic acid molecule or polypeptide molecule, as that term is used herein, is any piece that is shorter in length than the entire molecule. Preferably, a portion has a length sufficient to be characteristic of the full length molecule. For nucleic acid molecules, preferred portions are usually at least about 3-5 residues in length, more preferably at least about 5, 10, 15, 20, 25, 30, 35, 40, 45, 50, or 100 residues in length. For polypeptide molecules, preferred portions are typically at least about 2-5 residues in length, more preferably at least about 7, 10, 15, 20, 25, 30, or 40 residues in length.

"Primer"—The term "primer", as used herein, refers to a polynucleotide molecule that is characterized by an ability to be extended against a template nucleic acid stand, so that a polynucleotide strand whose sequence is complementary to that of at least a portion of the template strand, is produced linked to the primer. Preferred primers are at least approximately 5-10 nt long; particularly preferred primers are at least about 15 nt long. In many preferred embodiments, primers preferably have a length within the range of about 18-30 nt, preferably longer than approximately 20 nt.

DESCRIPTION OF CERTAIN PREFERRED EMBODIMENTS OF THE INVENTION

As described above, the present invention recognizes that vectors need not be provided as intact, discrete molecules, but rather can be provided as fragments that contain all or part of particular desired sequence elements. The invention provides techniques and reagents for the assembly of vectors (and/or inserts) through the linkage of such fragments. Certain preferred embodiments of this invention are described in more detail below.

Vector Elements

As will be appreciated by those of ordinary skill in the art, any desired nucleic acid sequence can be considered a vector element according to the present invention. Practitioners will be aware of their own needs and desires in terms of vector functions and attributes, and will readily be able to select appropriate sequences for use as vector elements. Nonetheless, certain types of sequence elements are already well established as useful in the field of vector construction. For example, Invitrogen Corporation, one of the larger distributors of molecular biology reagents, provides on its web site (www.invitrogen.com) a page entitled "Anatomy of a Vector" that lists the following categories of vector elements: promoters, inducible elements, transcriptional termination sequences, origins of DNA replication, affinity purification tags, multiple cloning sites/polylinkers, and selectable markers. The contents of this site, as they were presented on Jul. 19, 2000, are included herein as Appendix B.

Replication Elements

As described above, any sequence that operates to ensure replication of vector sequences in a selected host system constitutes a replication element. A variety of replication elements are already available in the art, and have been employed in commonly-available vector systems (see, for example, Ausubel et al., *Current Protocols in Molecular Biology*, Section II, Unit 1.5.1-1.5.17, John Wiley & Sons, 1998, the entire contents of which are incorporated herein by reference).

It will be appreciated by those of ordinary skill in the art that it is often desirable to construct a vector containing more than one replication element. For example, if it is desired that the same vector be able to replicate in more than one host cell type (e.g., in both bacterial cells and mammalian cells), then the vector should be designed to include replication elements that operate in each relevant cell type. On the other hand, it is also known that certain replication elements are incompatible with one another in a given cell type. It is generally desirable not to include incompatible elements in a single construct unless fragmentation of the construct in the host cell is desired.

Available replication elements that are known to operate in *E. coli*, the most commonly employed bacterium in molecular biology, include both high copy (so-called "relaxed control") elements such as pMB1 (100-300 copies/cell; Bolivar et al., *Gene* 2:95, 1977), ColE1 (>15 copies/cell; Kahn et al., *Method. Enzymol.* 68:268, 1979) and p15A (about 15 copies/cell; Chang et al., *J. Bacteriol.* 134:1141, 1978) and low copy (so-called "stringent control") elements such as pSC101 (about 6 copies/cell; Stoker et al., *Gene* 18:335, 1982), F (1 to 2 copies/cell; Kahn et al., *Method. Enzymol.* 68:268, 1979), and RK2 (2-4 copies/cell; Kahn et al., *Method. Enzymol.* 68:268, 1979). The R1 (low copy at 30° C. and high copy above 35° C.; Uhlin et al., *Gene* 22:225, 1983) replicon also operates in *E. coli*, as do various phage origins of replication including λ dv (Jackson et al., *Proc. Natl. Acad. Sci. USA* 69:2904, 1972), m13, f1, etc.

Replication elements that are known to operate in bacteria other than *E. coli* include RK2 and RSF1010, which have been shown, unlike ColE1, to have relatively broad host-ranges. In some cases, it may be desirable (or necessary) to introduce vectors into bacterial host cells through a mating process, in which case sequence elements encoding certain trans-acting factors (e.g., the tra or mob genes) may be required, as may be the cis-acting oriT site.

There are two primary categories of replication elements known to operate in yeast cells, centromeres and the 2µ replicon. Of course, since DNA can readily be targeted for integration in yeast cells, it is not always necessary for a vector to be used in yeast cells to include an origin of replication that is active in those cells. Sequences that target integration of the vector into other replicating nucleic acid molecules are sufficient to constitute a replication element according to the present invention in those circumstances.

Several viral origins of replication, such as simian virus 40 [SV40], bovine papilloma virus [BPV], and Epstein Barr Virus [EBV], oris are known to operate in mammalian cells (sometimes requiring the presence of additional viral genes) and therefore can be employed as mammalian replication elements according to the present invention. Alternatively, sequences sufficient to target integration of a vector into another nucleic acid molecule (e.g., a chromosome or virus) capable of replicating in the mammalian cell can be employed. Targeted homologous recombination has been demonstrated to work effectively in mammalian cells, so that regions of homologous gene sequence can operate as replication elements according to the invention. Analogously, sequence elements of the Cre recombinase system can be employed to direct integration of vector sequences in mammalian systems (see, for example, Fukushige et al., *Proc. Natl. Acad. Sci. USA*, 1992).

Viral origins of replication such as the baculovirus origin are known to operate in insect cells and can be employed as replication elements according to the present invention, as can other sequences, such as P-element sequences, that enable integration of vector sequences into other replication-competent nucleic acids.

Figure 2:
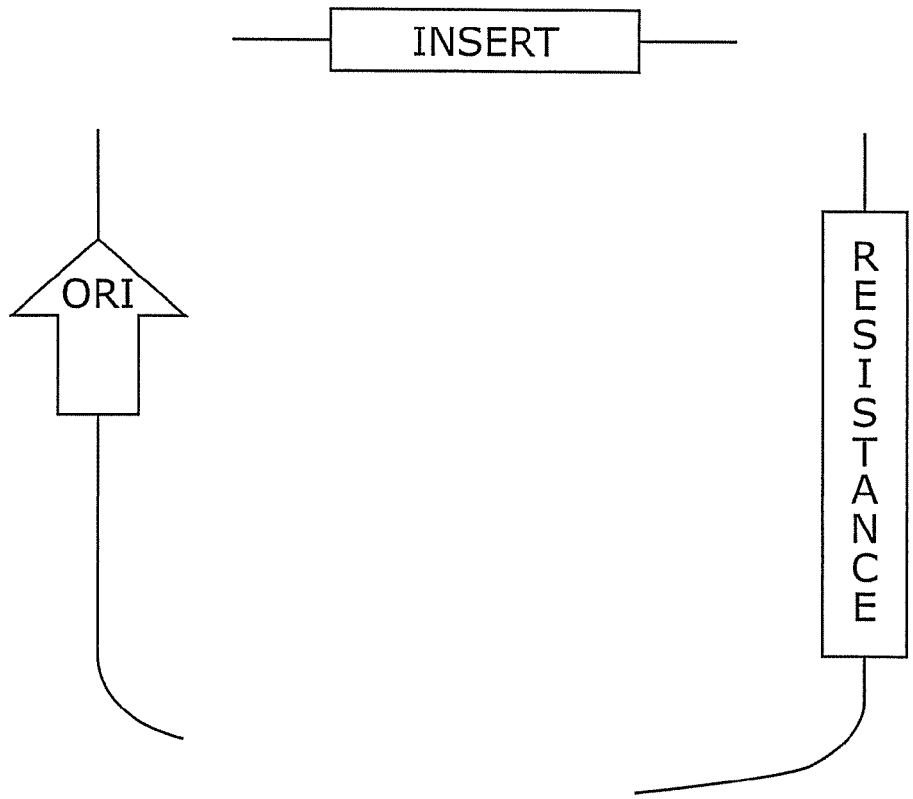
FIG. 2 shows assembly of a hybrid molecule comprising bacterial vector elements and an insert in a three-molecule linkage reaction according to the present invention.
Figure 3:
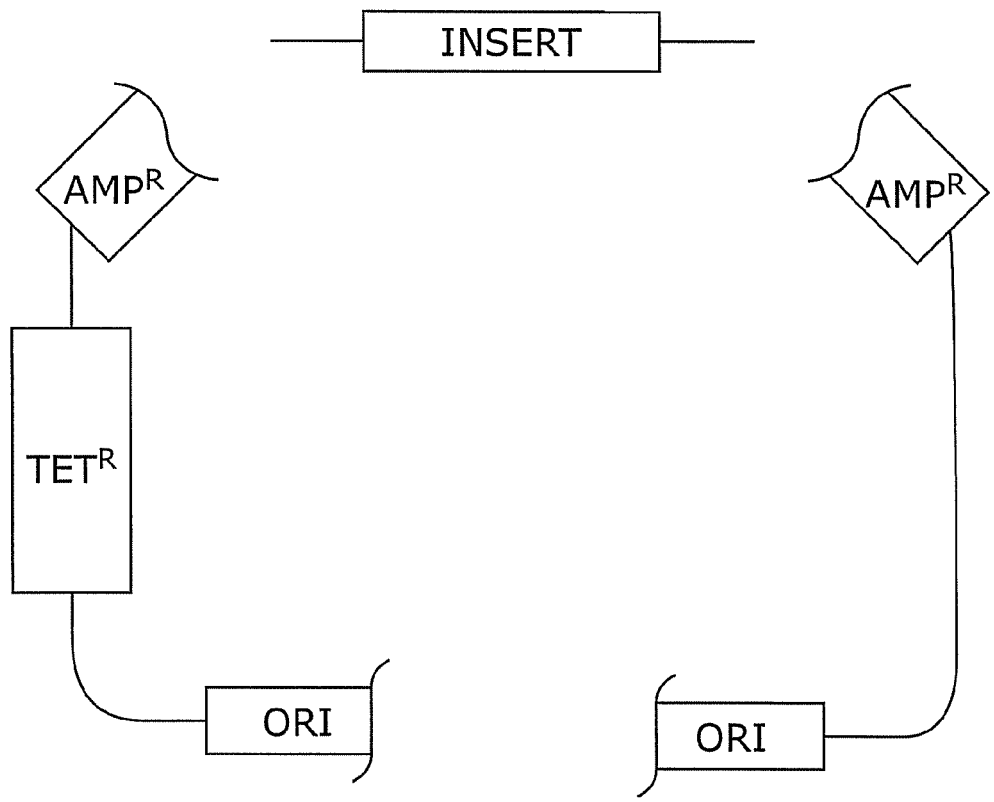
FIG. 3 depicts assembly of a hybrid molecule containing bacterial vector elements and an insert according to the present invention. Two vector fragments and one insert fragment are linked together to form a hybrid that can be selected by growth in the presence of tetracycline and lack of growth in the presence of ampicillin.
Figure 4:
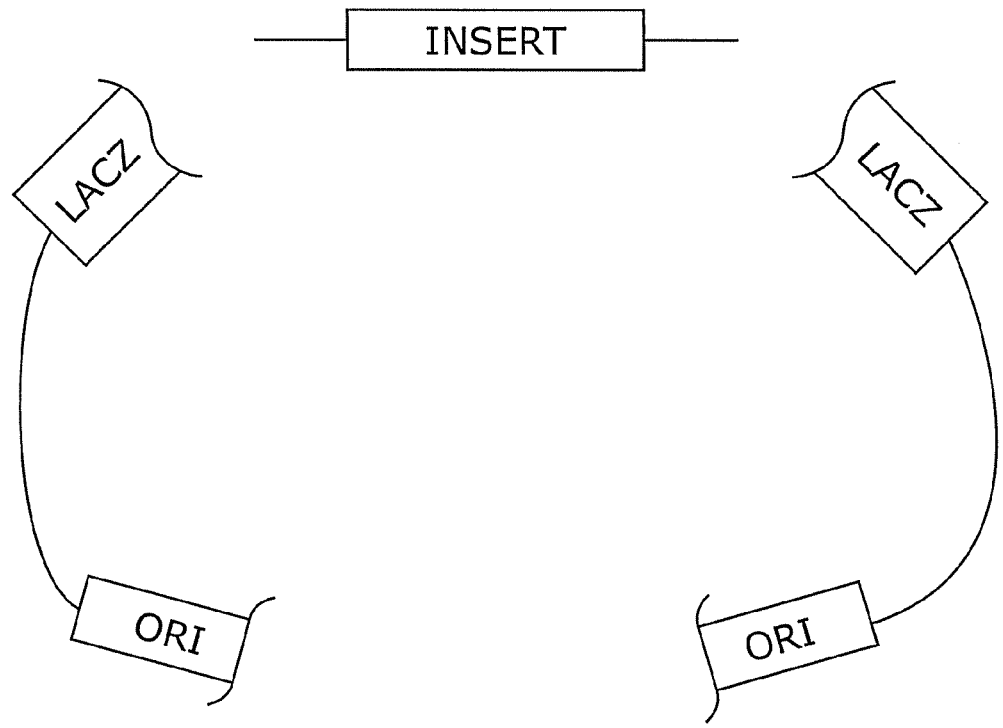
FIG. 4 depicts assembly of a hybrid molecule comprising bacterial vector elements and an insert according to the present invention. Two vector fragments, each of which contains a portion of a detectable element, and one insert fragment are linked together to form a hybrid. Hybrids that contain insert can be distinguished from those that do not by a blue/white screen.
Figure 5:
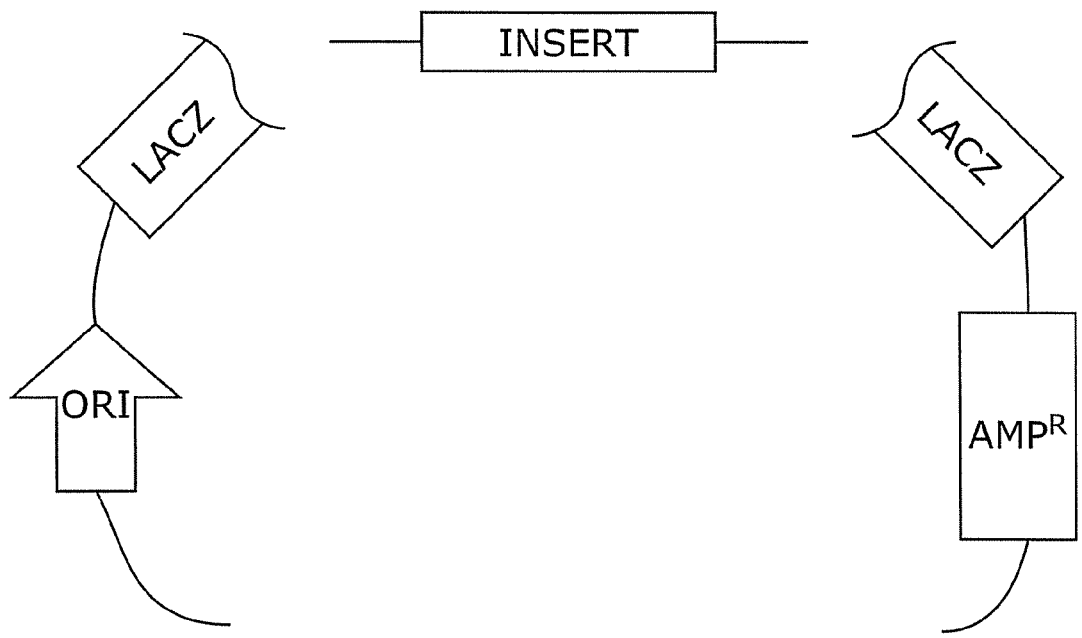
FIG. 5 shows assembly of a hybrid molecule containing bacterial vector elements and an insert according to the present invention. Two vector fragments, one of which contains a bacterial origin of replication and a first portion of a LacZ gene and one of which contains an ampicillin resistance gene and a second portion of the LacZ gene are linked to an insert fragment. Hybrids can be selected by growth in the presence of ampicillin; those containing insert can be distinguished from those lacking insert by a clue/white screen.
Figure 6:
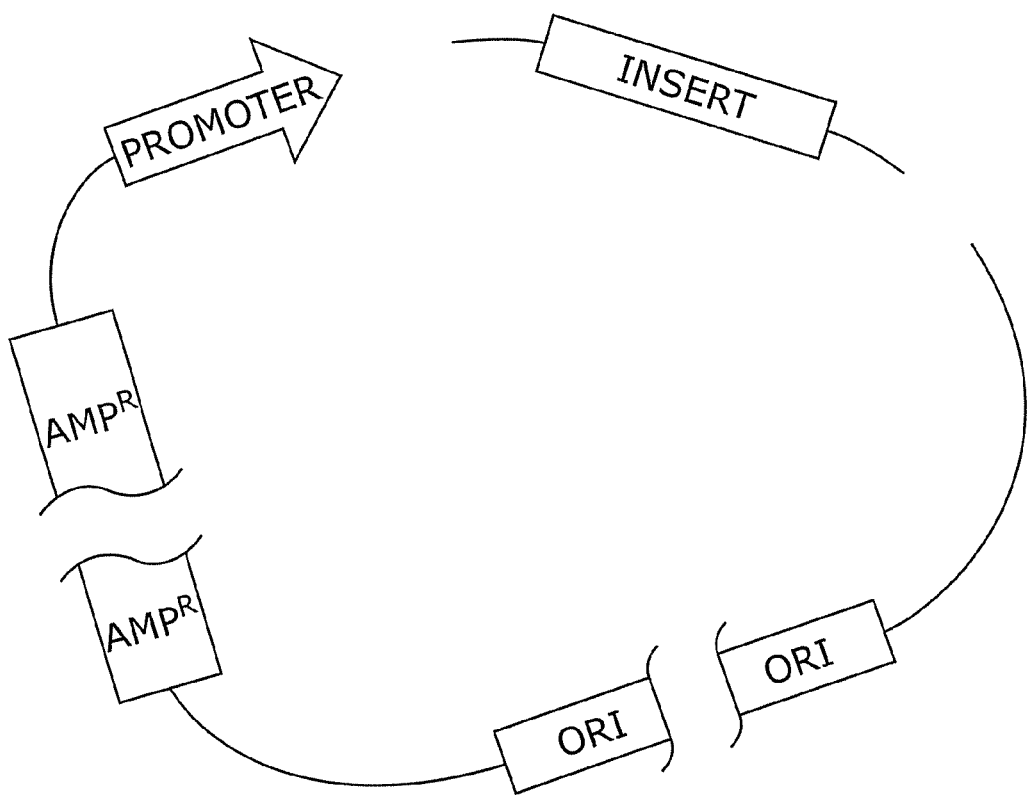
FIG. 6 shows assembly of a hybrid molecule from three vector fragments and one insert fragment. Linkage of the four fragments re-creates two vector elements, and operatively links a third (the promoter) with the insert sequences.
Figure 7:
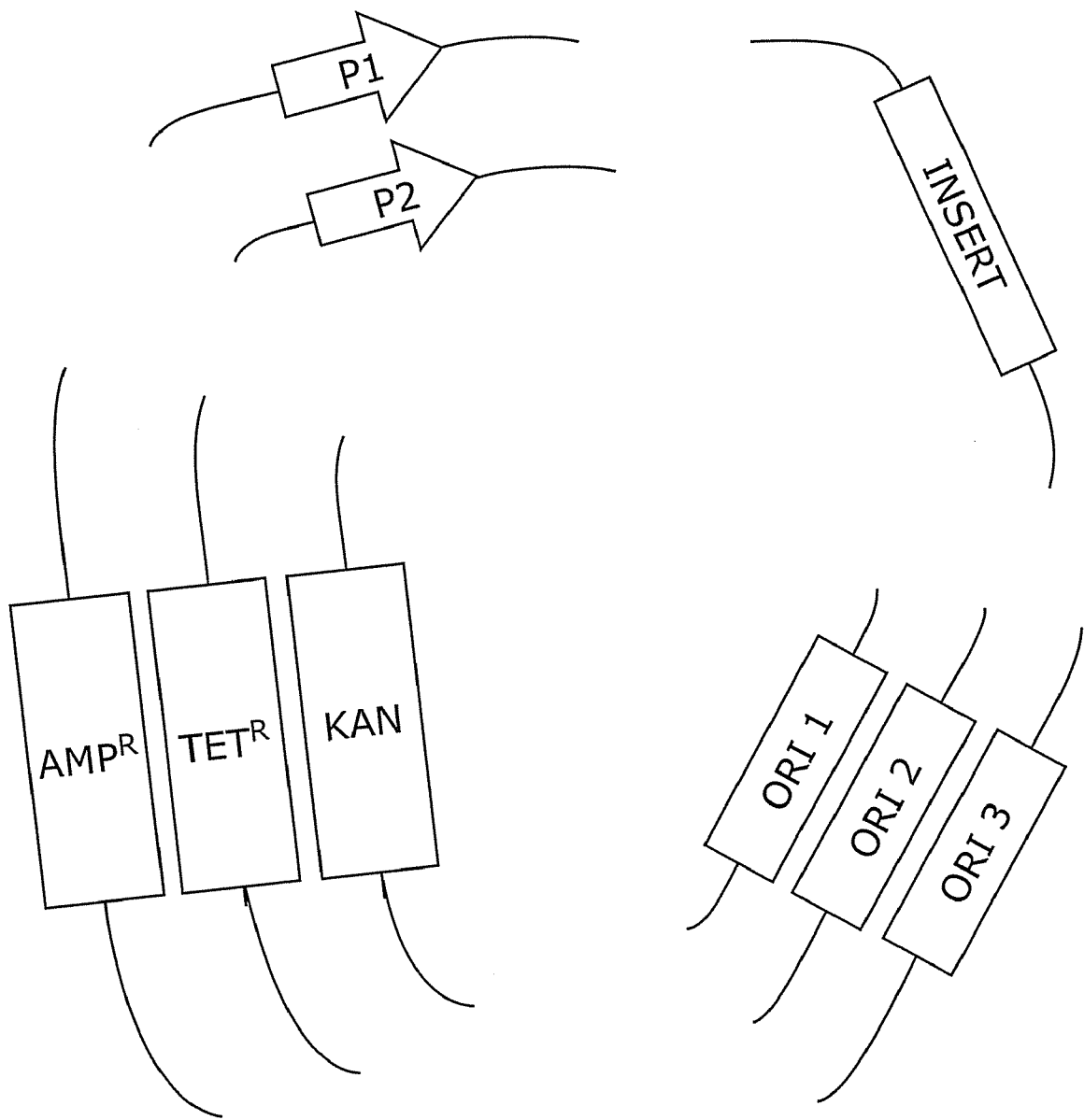
FIG. 7 shows collections of vector fragments, each of which contains only a single vector element, that may alternatively be linked to each other and an insert to form a hybrid molecule according to the present invention.
Figure 8:
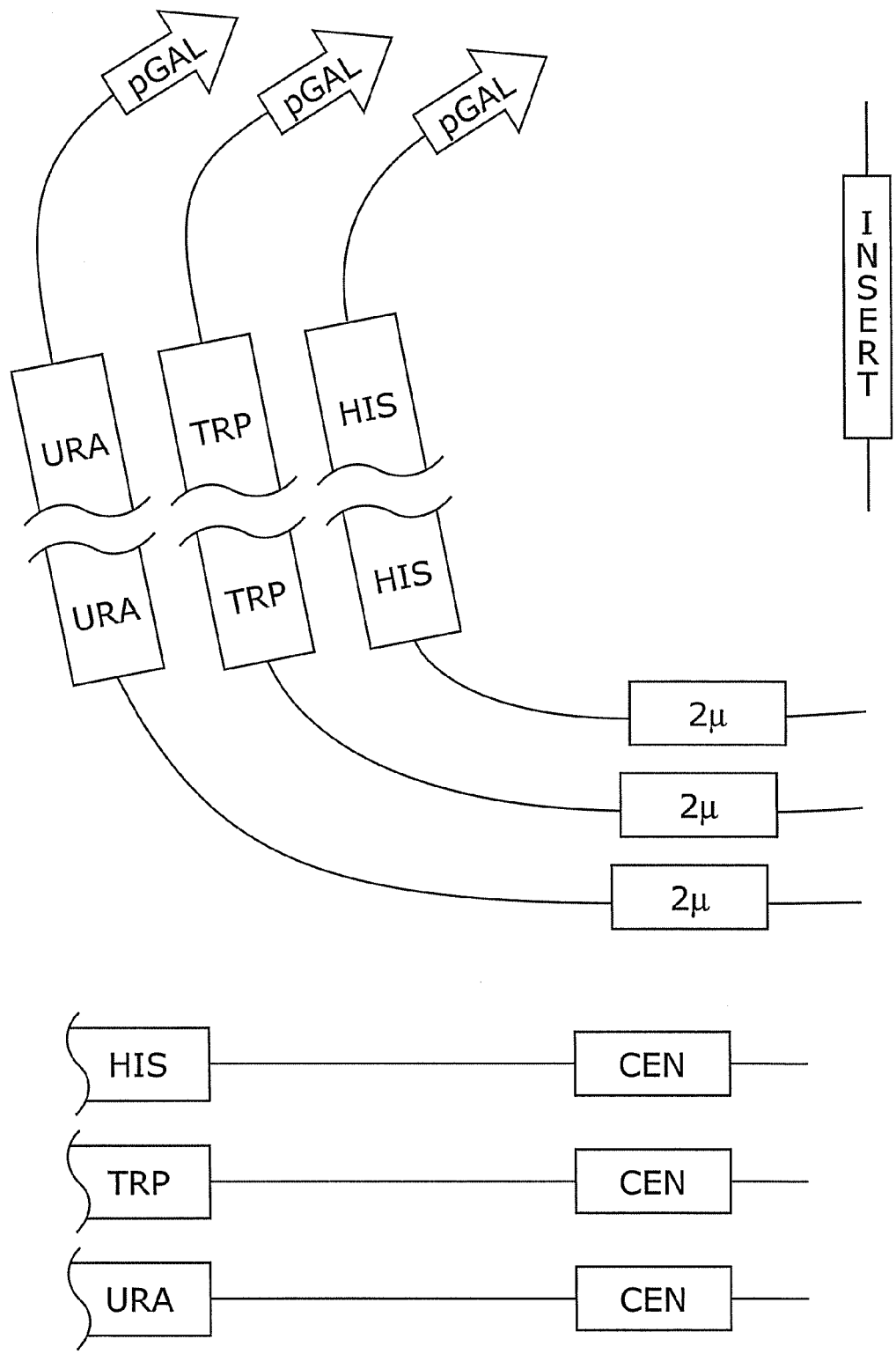
FIG. 8 depicts a kit comprising two collections of vector fragments that can be used in various combinations to create vectors with different attributes according to the present invention. The first collection of vector fragments contains three fragments, each of which includes the pGal promoter and a first portion of a selectable marker selected from the group consisting of the URA3, TRP1, and HIS3 genes. The second collection of vector fragments contains six different fragments, each of which contains a second portion of one of the selectable markers, and an origin of replication that is either a centromeric origin or a 2μ origin.

In certain embodiments of the invention, it will be desirable to provide a particular replication element in two parts, on two different fragments, so that hybrid molecules will only replicate if they contain properly ligated fragments (see, for example, FIGS. 3, 4, and 6). In other embodiments, replication elements are provided intact on a single vector fragment (see, for example, FIGS. 2, 5, and 7-9).

Vector Detection Elements

A wide variety of sequences are available that allow host cells containing vector to be distinguished from host cells that do not contain vector. There are two basic categories of such elements: those that contain a selectable marker (i.e., one that imparts a growth advantage to vector-containing cells under certain conditions) and those that contain a detectable marker. A wide variety of such markers is available, for use in different cell types.

The most commonly employed selectable markers utilized in bacterial systems are those that confer resistance to antibiotics such as ampicillin, chloramphenicol, kanamycin, and tetracyline. Similarly, selectable markers commonly utilized in insect and/or mammalian cells include those that confer resistance to zeocin, neomycin, blasticidin, or hygomycin. The DHFR gene, which confers the ability to grow in the absence of exogenous purines (and also confers resistance to methotrexate, can also be used as a selectable marker in a range of cell types including mammalian cells. Also, cytosine deaminase can be used as a selectable marker under conditions that require cells to convert cytosine to uracil for growth. Other selectable markers useful in mammalian cells include, for example, hygromycin-β-phosphotransferase (HPH), puromycin-N-acetyl transferase (PAC), thymidine kinase (TK), and xanthine-guanine phosphoriboseultransferase (XGPRT).

The most commonly employed selectable markers utilized in yeast cells include those that confer the ability to grow in the absence of a given nutrient such as uracil, tryptophan, histidine, leucine, lysine, etc.

Preferred detectable markers for use in accordance with the present invention include genes encoding proteins that produce detectable products. Commonly employed detectable markers include, for example, the β-galactosidase gene, the green fluorescence protein gene, the horse radish peroxidase gene, the nitric oxide syntheses gene, the chloramphenicol acetyl transferase gene, the luciferase gene, etc.

Those of ordinary skill in the art will readily appreciate that most or all of these vector detection elements can alternatively be employed as insert detection elements. For example, FIGS. 3-5 depict inventive reactions in which vector fragments are designed so that, if they become linked to one another, a vector detection element is created. On the other hand, if an insert fragment becomes linked between them, the vector detection element is not created. Thus, constructs containing the insert fragment and those not containing the fragment can readily be distinguished from one another.

Similarly, those of ordinary skill in the art will appreciate that it will often be desirable to design vector and/or insert fragments so that a vector detection element is only created if the fragments become linked together in the desired arrangement. FIG. 6, for example, depicts a particular embodiment of the invention in which this strategy was employed to simplify hybrid construct production according to the present invention.

It should be noted that one advantage of the present invention is that it renders the insert detection strategies described in the previous two paragraphs particularly practicable. The inventive modular approach to vector assembly, and particularly the inventive employment of cloning technologies that do not require restriction digestion, removes the need for a polylinker in order to introduce insert sequences into a vector. Since polylinkers add unnatural sequences, their location in the middle of a detectable or selectable gene typically disrupted the gene activity, so that it was not possible to use reverse selection or detection to assay for insert insertion. By contrast, the inventive technologies allow the seamless union of insert and vector sequences, making feasible the use of these convenient screens and selections.

Expression Elements

As will be appreciated by those of ordinary skill in the art, one of the most common uses of vector systems in molecular biology is to arrange for expression of insert sequences in a host cell of interest. Any sequence that participates in directing or regulating expression of a linked sequence can be an expression element according to the present invention. A wide variety of such sequences are known in the art; certain examples are discussed in more detail below.

PROMOTER: Promoters are the regions of DNA that are responsible for establishing the initiation site for transcription. A variety of different promoters, operative in different systems, have been defined and characterized. Different promoters may direct expression of linked sequences at different levels. Furthermore, some promoters are constitutively active, while others can have their activity modulated through adjustment of the experimental conditions. Some promoters are active in only particular cell types, where as others are ubiquitously expressed.

Preferred promoters known to be active in bacterial cells include, for example, $P_{BAD}$, $P_L$, $P_R$, lack, tack, trc, spa lacUV5, T3, T7, T7 LAC, SP6, etc.; preferred promoters known to be active in yeast cells include, for example pGAL1, pAOX1, pADH, etc.; preferred promoters known to be active in insect cells include, for example, the MT, Ac5, and polyhedrin promoters, etc; preferred promoters known to be active in mammalian cells include, for example, $P_{AHSP}$, $P_{SG}$, $P_{CMV}$, $P_{EF-1\alpha}$, $P_{SV40}$, $P_{RSV}$, $P_{PGK}$, $P_{MMTV}$, $P_{MMTV}$, $P_{MC1}$ etc.

ENHANCERS/TRANSCRIPTIONAL REGULATORS: Regulator sequences that operate to stimulate or repress transcription from a given promoter in certain cell types or under certain conditions can often be combined with any of a variety of different promoters to create a transcription control element with useful characteristic. The universe of known regulatory sequences operative in different organisms is very large. Particularly preferred elements that are commonly used in vector systems include, for example, the lac operon, the λ cI site, the tet operon, lexA sites, Gal4 sites, the SV40 enhancer, the MMTV enhancer, etc. Those of ordinary skill in the art will immediately recognize the huge range of alternative sequences that could be employed in the practice of the present invention. Experiments to define additional such sequences, operative in the context of any particular experiment, are routine.

TRANSCRIPTION TERMINATOR: Although not required, it is sometimes desirable to include in an expression vector sequences that will terminate transcription of relevant sequences at a selected point. Without such termination signals, it may be possible for RNA polymerases, at least under some circumstances, to transcribe indefinitely around a circular construct. A variety of different transcriptional termination sequences have been identified; the one most commonly used in vector applications is probably the SV40 terminator. Alternatively or additionally, 3'-end formation signals, such as polyadenylation sites, may be employed.

SPLICING SIGNALS: In certain circumstances, it may be desirable to include in inventive expression vectors signals that can direct splicing of transcripts encoded by insert sequences. For example, if a vector includes a promoter and exonic sequences including a splice donor site, then insert sequences containing a splice acceptor site can be expressed and translated. In certain embodiments of the invention, it might be desirable to provide a collection of vectors or vector fragments (3) that contain the splice acceptor site in all three possible frames, so as to ensure in-frame fusions of insert sequences in one version of the vector, regardless of whether information about the insert sequence is available.

TRANSLATION START: Often, if expression of an insert that does not include 5' sequences (or is not known to include such sequences) is desired, it will be useful to include translation start sequences. The consensus translation start sequence, known as the Kozak sequence, will provide the strongest translation initiation signal, but in most cases a single ATG reasonably positioned with respect to the start of the transcript will suffice.

TRANSLATION STOP: Expression vectors designed to express insert sequences that may be lacking their natural 3' ends often benefit from the inclusion of translation stop sequences. As with the translation start and splicing sequences, families of vectors can be prepared containing the relevant sequences in all three possible frames so that knowledge of the insert sequence is not required. Alternatively, a single vector could be employed but families of insert fragments can be prepared with additional (or fewer) nucleotides on one or both ends.

Gene Fusions

As those of ordinary skill in the art will be aware, a variety of vector systems have been engineered to generate gene fusions between insert sequences and a reporter gene in the vector backbone. Such fusions are useful, for example, to detect expression patterns of the insert sequences, or to detect expression control elements that may be present in the insert sequences. Gene fusions may also allow a researcher to track the expression products of the fused gene.

Particularly preferred detectable genes for use in gene fusion applications include, for example, LacZ, chloramphenicol acetyl transferase (CAT), green fluorescence protein (GFP), luciferase, horse radish peroxidase (HRP), etc.

Fusion Proteins

One version of gene fusions that is particularly commonly employed in vector systems is fusions that generate fusion proteins with a desirable characteristic. As will be appreciated, it will often be desirable to provide families of vectors or vector fragments that allow C-terminal, N-terminal, or internal fusions, and also that allow fusions in all possible frames, preferably without knowledge of insert sequence.

For example, a variety of sequence elements are available that encode polypeptides that, when fused to a polypeptide encoded by an insert sequence, allow that polypeptide to be readily purified. Particularly preferred purification tags include, for example, $(His)_6$, thioredoxin, glutathione-S-transferase, streptavidin, staphylococcal protein A (which interacts strongly with IgG; Amersham Pharmacia Biotech, Piscataway, N.J.), etc.

Also available are a variety of sequence elements encoding detectable moieties, such as epitopes for which high-specificity antibodies are available, that can be useful in the detection of an expression fusion protein. Examples of such detectable epitopes include, for example, Xpress™, c-myc, CA25, thioredoxin, V5, HA, calmodulin binding peptide (CBP), Aag, etc.

In some cases, it is desirable to remove the protein tags created by fusion of encoding insert sequences with encoding vector sequences. Sequence elements encoding polypeptide cleavage elements (e.g., by furin, enterokinase, thrombin, factor X1, PreScission, etc.) are particularly useful in such applications.

Other useful sequence elements for the production of fusion proteins are ones that encode targeting moieties, such as secretion signals (e.g., BiP for insect cells, human placental alkaline phosphatase or human growth hormone for mammalian cells, protein A for bacterial cells, etc.) or other elements, that direct the fusion product to a particular cellular location. Examples of such targeting sequences include, for instance, yeast AgA2 sequences that target the fusion protein to the cell surface, VP22 fusions that target to the mammalian nucleus, pRLT3-NLS, COXVIII signal, etc.

Polylinkers

One virtually ubiquitous element in most commercially-available vectors today is a so-called "polylinker" or "multiple cloning site". In certain embodiments of the invention, it may be desirable to include vector fragments containing such elements in linkage reactions. However, in many embodiments, it will be desirable to create fragments and/or hybrid molecules without employing the use of restriction enzymes. As techniques for such restriction-free nucleic acid manipulation become more accepted, the need for polylinkers in inventive vectors and reactions will diminish.

Other Elements

Those of ordinary skill in the art will readily appreciate that any of a variety of other sequence elements may be included in vector fragments according to the present invention. The foregoing has been intended to provide merely a sampling of certain examples of sequence elements that are currently commonly found in vector sequences. One of the advantages of the present invention is that, by providing techniques and reagents that allow the ready production of specifically designed vectors through the assembly of prepared fragments, it is expected that the invention will also help researchers expand the range of sequence elements utilized in vector applications.

Insert Elements

As will be apparent to those of ordinary skill in the art, any nucleic acid sequence may be employed as an insert element according to the present invention. A researcher may choose any sequence or sequences s/he likes to be linked to vector sequences. Also, more than one insert element may be employed. Furthermore, each insert element may be provided as a single insert fragment, or may be distributed over multiple insert fragments that will be linked together in series in the final hybrid product. In certain embodiments of the invention, part or all of a given insert element may even be prepared as a single fragment that also includes part or all of one or more vector elements. Any collection of contiguous insert sequences is considered a single insert element for the purpose of the present invention.

Those of ordinary skill in the art will recognize that the classification of particular sequences as "insert elements" as compared with "vector elements" is not critical to the invention. In fact, the inventive recognition that a "vector" need not be a single discrete molecular entity in a sense renders such distinctions arbitrary. Nonetheless, both the concept and the terminology of a "vector backbone" and an "insert" are well established in molecular biology and therefore can be useful for the purposes of clarity and communication.

Preparation and Linkage of Fragments

In general, any method may be used to prepare fragments for hybridization and/or linkage according to the present invention. However, it is preferred that, for each hybrid molecule to be assembled, at least one fragment is prepared without the use of restriction enzymes, and preferably without the use of any endonuclease.

In certain preferred embodiments of the invention, fragments are prepared in a form that allows them to be linked together by ligation. In other embodiments, fragments are prepared in a manner that allows them to be linked together by splicing. In particular, U.S. patent applications U.S. Ser. Nos. 08/814,412, 09/399,593, 09/225,990, and PCT/US00/0189, and U.S. Pat. Nos. 5,498,531 and 5,780,272, each of which is incorporated herein by reference, contain thorough descriptions of methods and strategies useful in the preparation of nucleic acid (RNA or DNA) fragments that contain flanking intronic sequences and can be linked to one another by trans- or cis-splicing. In yet other embodiments, fragments are prepared in a form that allows topoisomerase-mediated linkage.

Often, it will be desirable to prepare fragments so that, for each linkage reaction to be performed in the assembly of a hybrid molecule, the fragments are designed to associate with one another in only one way and to produce only a single major linkage product. For example, fragments may be prepared so that each has single-stranded overhangs on one or both ends, and only fragments that are to be adjacent to one another in a hybrid molecule have complementary overhangs. Alternatively or additionally, fragments may be engineered to include intronic elements that are only compatible with the intronic elements on adjacent fragments. Such "directed linkage" (i.e., linkage in only one arrangement) of fragments discussed above is particularly desirable where multiple fragments (i.e., three or more, preferably four or more, and more preferably five or more) are to be linked together in a single linkage reaction. For linkage reactions containing small numbers of fragments (2 or 3), directed linkage can be assured by controlling the phosphorylation state of the relevant fragment ends.

In other preferred embodiments of the invention, it may be desirable to prepare fragments so that they can become linked to one another in any of a variety of different ways. This phenomenon is referred to herein as "linkage degeneracy". In such embodiments, a single linkage reaction can generate a "library" of different hybrid molecules that can subsequently be distinguished and/or separated from one another as desired.

In yet other preferred embodiments of the invention, fragments can be designed for directed ligation as described above, but then multiple alternative versions of each particular fragment can be provided in the same linkage reaction so that, once again, a library of hybrid molecules is produced in a single linkage reaction. This phenomenon is referred to herein as "selection degeneracy". For example, fragments A, B, and C can be designed and prepared so that they can only be linked to one another in the arrangement ABC (which can be a linear or a circular arrangement). If multiple different A fragments (e.g., A1, A2, A3, ... An), multiple different B fragments, and/or multiple different C fragments are employed in a single linkage reaction, then a library of different hybrid molecules, each having an ABC structure, will be produced in that reaction (e.g., A1B17C3, A1B1C1, A1B2C1, etc.). Those of ordinary skill in the art will readily appreciate that the different versions of the A fragment need not bear any relationship to one another other than being designed to be link only to a B fragment, etc. Alternatively, each version of a given fragment could, for example, contain different varieties of the same vector element(s) or element portion(s) (e.g., different drug resistance genes).

Still other preferred embodiments combine the two kinds of degeneracy discussed above, so that a single linkage reaction may create a library of hybrid molecules in which both the arrangement and selection of fragments is varied.

According to the present invention, particularly preferred fragments for use in accordance with the present invention contain one or more single-stranded overhangs available for hybridization with complementary overhangs on other fragments. It is most preferred that such overhang-containing fragments be prepared without the use of restriction enzymes. It is particularly preferred that such fragments be prepared using RNA-Overhang Cloning (ROC) or DNA-Overhang Cloning (DOC), as described for example in U.S. Ser. No. 09/225,990; PCT US00/00189; and U.S. Ser. No. 09/478, 263, each of which is incorporated herein by reference in its entirety (see also Examples 5-8).

Once a hybrid molecule is created by hybridization or linkage of vector and/or insert fragments, it may be replicated by any available in vitro or in vivo mechanism. In certain preferred embodiments of the invention, hybridization or linkage reactions themselves, or isolated or purified hybrids prepared from such reactions (e.g., by gel electrophoresis), may be directly transformed or transfected into host cells (or otherwise introduced into a host system). In some cases, it may be desirable to perform one or more manipulations prior to introducing a hybrid molecule into a host cell. For example, linkage of two fragments created using some embodiments the ROC methodology will produce a hybrid molecule that includes some regions of double-stranded RNA that may not be stable inside certain host cells. Accordingly, it may be desirable to perform at least a single round of DNA replication of such a hybrid prior to introducing it into a cell. Other circumstances in which such additional manipulations (e.g., nick repair, etc.) are desirable will be apparent to one of ordinary skill in the art.

Kits

As discussed herein, one aspect of the present invention comprises the recognition that vectors are comprised of modular elements and can be assembled from individually prepared fragments. One part of this recognition includes the realization that vector fragments can be provided as isolated cassettes, ready to be assembled by a user or a manufacturer.

In one embodiment of the invention, a variety of different possible vector elements is offered to a user who selects particular pieces of interest. Fragments that together comprise these pieces are then prepared and are provided to the user for assembly into a vector. Optionally, reagents for performing the assembly (e.g., ligase if the fragments are prepared with overhangs amenable to linkage by ligation; splicing reagents if the fragments are prepared for linkage by splicing; etc.). Alternatively, the fragments may be linked together into a "designer vector" before being provided to the user.

In other embodiments of the invention, kits are provided that contain multiple optional fragments, each of which contains a selected vector element or elements, or fragment(s) thereof, so that a user can readily assemble any of a variety of different vectors my mixing different collections of fragments together in linkage reactions. For example, a bacterial expression vector kit could be provided that contains (a) a first collection of first fragments, each of which contains the pTac promoter and also contains a portion of an antibiotic resistance gene, where different fragments in the collection contain portions of different antibiotic resistance genes; (b) a second collection of second fragments, each of which contains the remainder of one of the antibiotic resistance genes and also contains the ColE1 origin of replication; and (c) ligation reagents. A user could then select particular first and second fragments that, when ligated with his or her chosen insert fragment(s), would create a hybrid containing a chosen antibiotic resistance gene and the insert element under control of the pTac promoter. Those of ordinary skill in the art will immediately recognize the infinite variety of related other kits that could alternatively or additionally be provided.

The inventive recognition of vector modularity also provides a new perspective on valuable reagents, and systems for providing such reagents to users. For example, in addition to kits as discussed above, reagent providers could prepare catalogs or menus (either paper or electronic) from which users can select particular desired vector elements or fragments. In certain preferred embodiments of the invention, the catalog or menu is presented on a World Wide Web site that the user can access and through which the user can place an order. In other embodiments a paper form is provided, or information about telephone contact is provided. As discussed above, selected fragments may be provided to the user as isolated fragments, as fragment collections, as linked pieces (e.g., complete vectors), as kits (e.g., including linkage reagents, purification reagents, amplification reagents, instructions for use and/or other relevant materials), or in any other desirable form. The invention therefore provides, in addition to the various techniques and reagents discussed herein, new methods of doing business in the area of molecular biology reagents.

Hybrid Molecules

As discussed herein, the techniques and reagents provided by the present invention allow the ready assembly of any of a variety of hybrid molecules, generated by hyrbidization and/or linkage of vector and/or insert fragments. In some embodiments of the invention, a vector is assembled from vector fragments (via one or more than one linkage reactions) prior to linkage of vector sequences with insert sequences. In other embodiments, assembly of the complete, final hybrid product is accomplished in a single linkage reaction. In other embodiments, one or more linkage fragments is/are linked to one or more vector fragments in a first linkage reaction, and one or more additional linkage reactions are subsequently performed to add additional vector and/or insert fragments. Each and every hybrid molecule produced in such a linkage reaction is encompassed within the scope of the present invention.

EXAMPLES

Example 1

Assembly of a λ Vector/Insert Hybrid

FIG. 1 presents an inventive reaction for the assembly of a hybrid molecule containing two λ phage arms (a λ cloning vector) separated by a chosen insert. As is well known, λ vectors are particularly useful for the cloning of relatively large (up to about 50 kB) fragments. The insert-containing hybrids can be packaged (typically through the use of helper phages) into phage heads in vitro. Although the efficiency of packaging can be relatively low (around 10%), the subsequent efficiency of genome transfer into bacteria through infection is close to 100% (see, for example, Ausubel et al., *Current Protocols in Molecular Biology*, Unit 1.10, Current Protocols, 1987, the entire contents of which are incorporated herein by reference).

Example 2

Assembly of a Bacterial Vector/Insert Hybrid

FIG. 2 presents an inventive reaction for the assembly of a hybrid molecule containing a bacterial origin of replication, an antibiotic resistance gene, and a chosen insert. The hybrid molecule is assembled by linkage of three fragments, each of which contains a single element. Preferably, the fragments are prepared to have complementary overhangs selected to provide for directional ligation. Alternatively, the indicated element in each fragment may be flanked by intronic components that direct appropriate trans-splicing reactions in vivo or in vitro.

Example 3

Assembly of a Bacterial Vector/Insert Hybrid in which the Insert Disrupts a Detectable Element The inventive reaction depicted in FIG. 3 differs from that shown in FIG. 2 (and discussed above in Example 2) in at least two ways. First, the two vector fragments employed in the reaction of FIG. 3 each contain a part of the bacterial origin of replication, so that only hybrid molecules in which these two fragments are properly linked together will be able to replicate in bacteria. Also, each vector fragment contains a portion of the ampicillin resistance gene. If a hybrid is assembled that does not include an insert, the ampicillin resistance gene will be re-created (unless some mutation occurs) and bacteria containing the resulting hybrid will be resistant to both tetracycline and ampicillin. By contrast, the ampicillin gene will not be re-created in hybrid that do contain the insert. Thus, bacteria containing complete hybrids will be distinguishable from those containing partial hybrids that lack insert because those containing complete hybrids will be resistant to tetracycline but not ampicillin, whereas those containing partial hybrids will be resistant to both.

The strategy depicted in FIG. 3 is particularly useful for fragments that do not have directionally specific ends. For example, if blunt-ended fragments are to be employed, or if the both ends of the insert fragment (and both ampicillin fragment ends) contain identical overhangs, the ability to identify desirable hybrids from the universe of possible hybrids is particularly useful.

The strategy depicted in FIG. 4 is analogous to that depicted in FIG. 3 except that hybrids containing insert are distinguishable from those lacking insert on the basis of a blue/white screen rather than a growth/no growth screen.

The strategy depicted in FIG. 5 is also similar, except that linkage of the vector fragments is not required to create a functional origin of replication. For this strategy, it is generally preferred that at least the vector fragments be engineered for directional linkage, so that they can only be linked to one another in a single orientation.

Example 4

Assembly of a Hybrid Bacterial Expression Vector/Insert Construct by 4-Way Ligation The inventive strategy depicted in FIG. 6 shows simultaneous linkage of three different vector fragments with an insert fragment. A hybrid vector molecule containing both an origin of replication and an ampicillin resistance gene can only be assembled through proper linkage of the three vector fragments. Thus, selection strategies can be employed to identify desirable hybrid molecules. Such molecules can then be screened for expression of the insert in order to identify those that are complete as compared with those that contain only vector sequences.

Example 5

Assembly of a Hybrid Bacterial Vector/Insert Molecule Using DOC

Figure 9B:
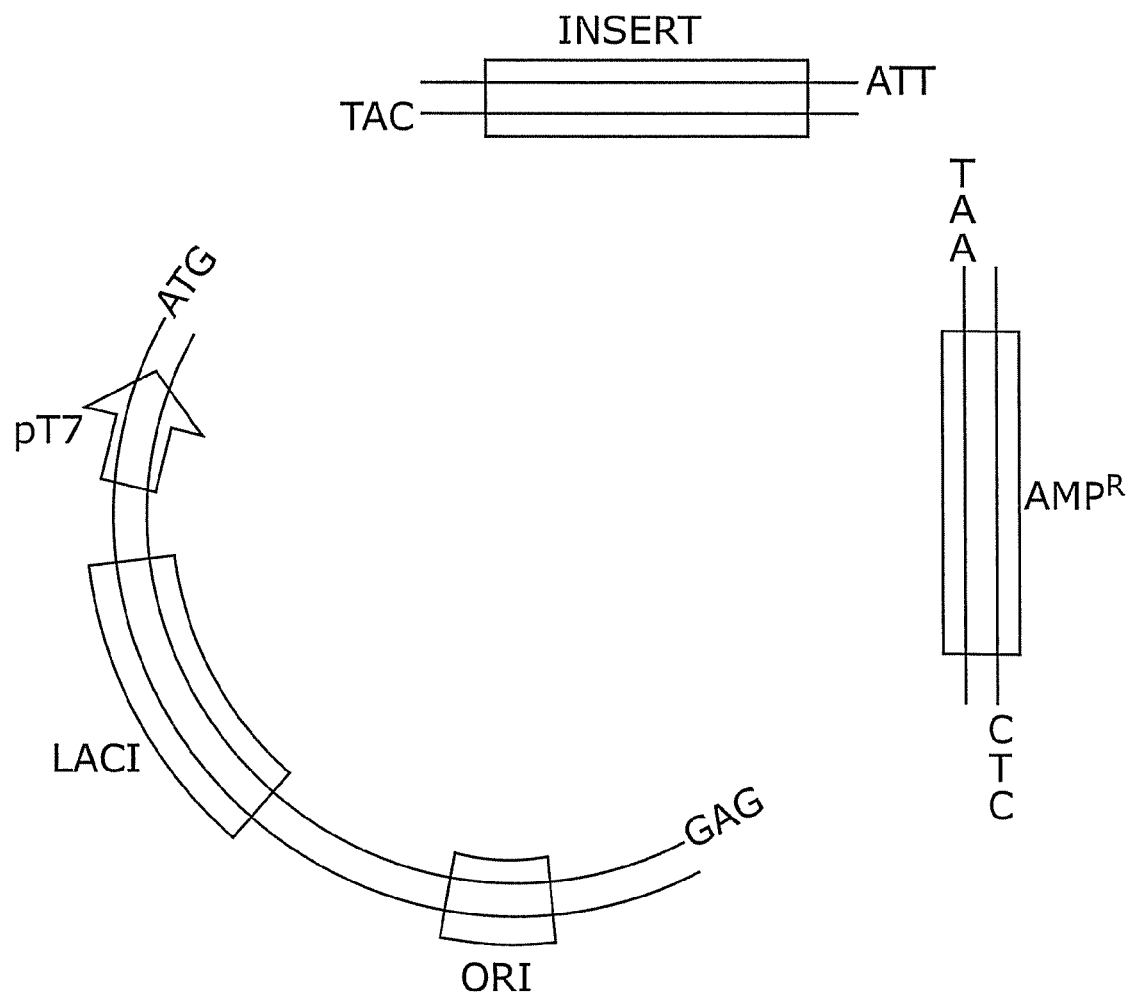
FIG. 9 depicts assembly of a hybrid molecule from two vector fragments and one insert fragment, each of which was prepared by DOC, according to the present invention. Panel A shows the generation of the two vector fragments; Panel B depicts the ligation of these two fragments with the insert fragment to produce the final hybrid.

The inventive scheme depicted in FIG. 9 was carried out as follows. Vector fragments were amplified from the pET 19b vector (Novagen, Madison, Wis.) using the following primers (lower case letters indicate RNA residues; upper case letters indicate DNA residues): EV-1 (5'-cauGGTATATCTCCT-TCTTAAAG; SEQ ID NO:1), EV-2 (5'-cucATGAC-CAAAATCCCTTAAC; SEQ ID NO:2), EV-3 (5'-gagAT-TATCAAAAAGGATCTTC; SEQ ID NO:3), and EV-4 (5'-uaaCTAGCATAACCCCTTGG; SEQ ID NO:4). EV-1 and EV-2 were used together to generate vector fragment 1, containing the bacterial origin of replication, the LacI gene, and the pT7 promoter; EV-3 and EV-4 were used together to generate vector fragment 2, containing the Amp gene.

In a separate DOC reaction, an insert fragment containing the Lac Z gene was amplified from the pBluescript II SK (−) vector (Stratagene, La Jolla, Calif.), with primers 5' Lac Z (5'-augACCATGATTACGCCAACG; SEQ ID NO:5) and 3'Lac Z (5'-uuaCAATTTCCATTCGCCATTC; SEQ ID NO:6). 100 μl PCR reactions contained 5 ng of template DNA, 1× cloned PFU buffer (Stratagene, La Jolla, Calif.), 1 mM MgSO$_4$ 200 μM of each dNTP, 1.45 U cloned PFU (Stratagene), 1.25 U PFU Turbo™ polymerase and 50 pM of each primer. Reactions were performed in a Robocycler (Stratagene, La Jolla, Calif.) as follows: 1 cycle 95° C., 5 min; 53° C., 3 min; 72° C., 6 min (10 min for vector fragment 1); 30 cycles, 95° C., 1 min; 53° C., 1 min; 72° C., 3 min (8 min for vector fragment 1); and 1 cycle 72° C. 10 min.

Products of the PCR reactions were separated on a 1% agarose gel, and purified using the GENECLEAN II kit (Vista, Calif.). 12 μl of each purified fragment was placed separately in 1× first strand buffer (Life Technologies, Rockville, Md.) with 10 mM DTT, 5 mM of each dNTP, and 200 U M-MLV (Life Technologies). Reactions were incubated for 20 min at 42° C. Reactions were then placed at 70° C. for 10 min to heat kill the enzyme.

Primer ribonucleotides were removed from the PCR products by hydrolysis with NaOH. 6 μL of 1 N NaOH were added to each reaction, and the mixtures were incubated for 30 min at 45° C. 6 μl of 1 N HCL, 4 μl of 10× ligase buffer (USB, Cleveland, Ohio), and 10 U of T4 PNK (USB) were then added. Reactions were incubated at 37° C. for 30 min. Phosphorylated fragments were combined in equimolar amounts (approximately 50 ng) and ligated with 10 U of T4 DNA ligase (USB) at 25° C. for 2 hrs. 5 μl of the ligation reaction was then transformed into *E. coli*.

Example 6

Assembly of Hybrid Vector/Insert Molecules Using ROC with Internal Terminators

We prepared hybrid vectors containing an origin of replication (Ori) fragment and a kanamycin resistance gene (KAN) fragment, by amplifying each fragment with primers that contained one or more residues not copied by the DNA polymerase utilized in the reaction (i.e., "terminator" residues). The Ori fragment was amplified from pET19b (Novagen, Madison, Wis.); the KAN fragment was amplified from pCR 2.1 (Invitrogen, Carlsbad, Calif.). FIG. 11 shows the various primers used and fragments generated. As will be seen, some reactions generated a 2400 bp ori fragment; others generated an 824 bp fragment, (denoted "Ori(s)" because it is smaller). The smaller fragment, Ori(s), lacks an 11 pb direct repeat that can create a deletion hotspot when it is present.

PCR reaction cycling, product annealing and *E. Coli* transformation were performed as described in Examples 7 and 8.

Example 7

Figure 10:
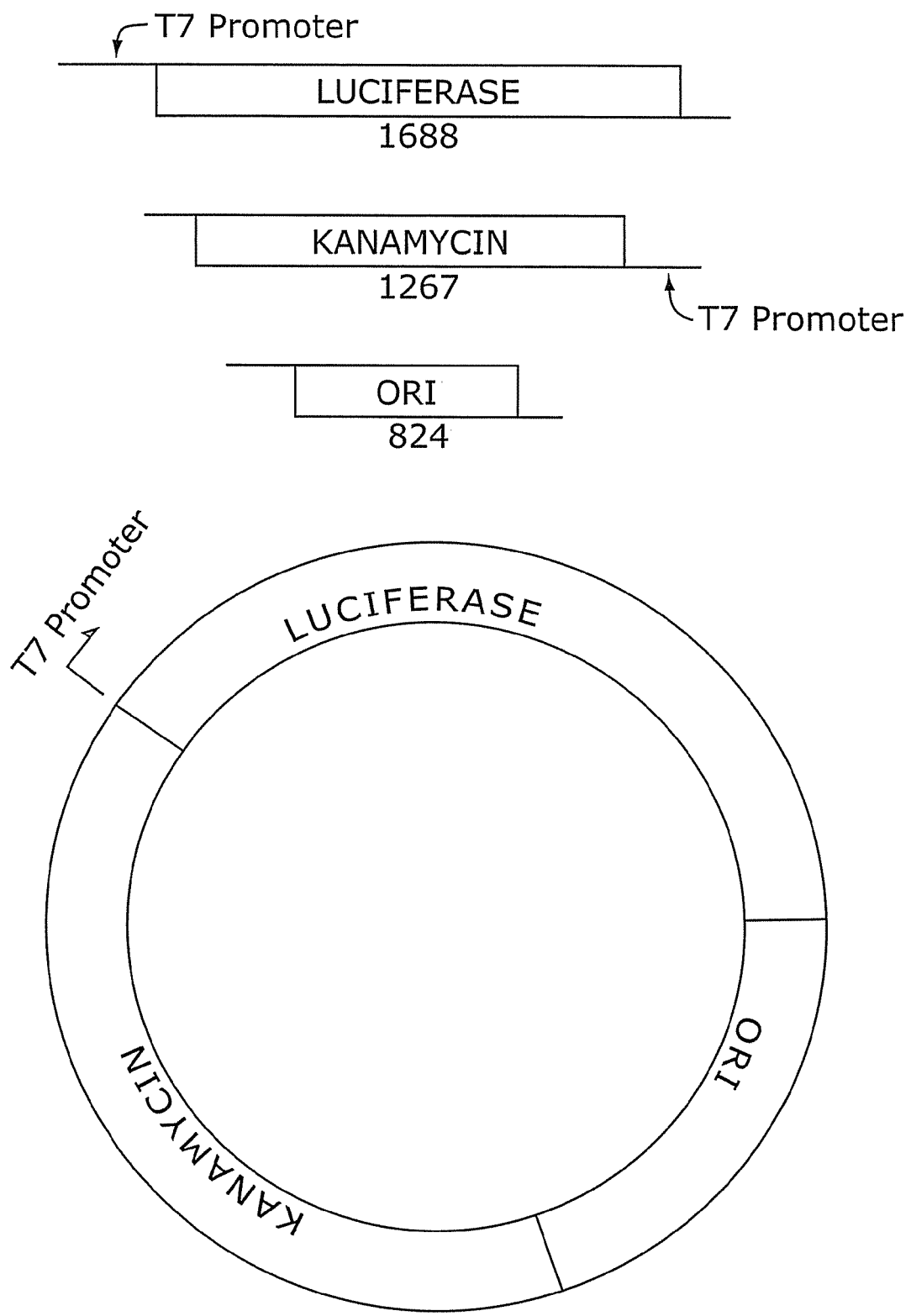
FIG. 10 shows a hybrid molecule assembled from two vector fragments and are insert fragment, each of which was prepared by DOC, according to the present invention.
Figure 12:
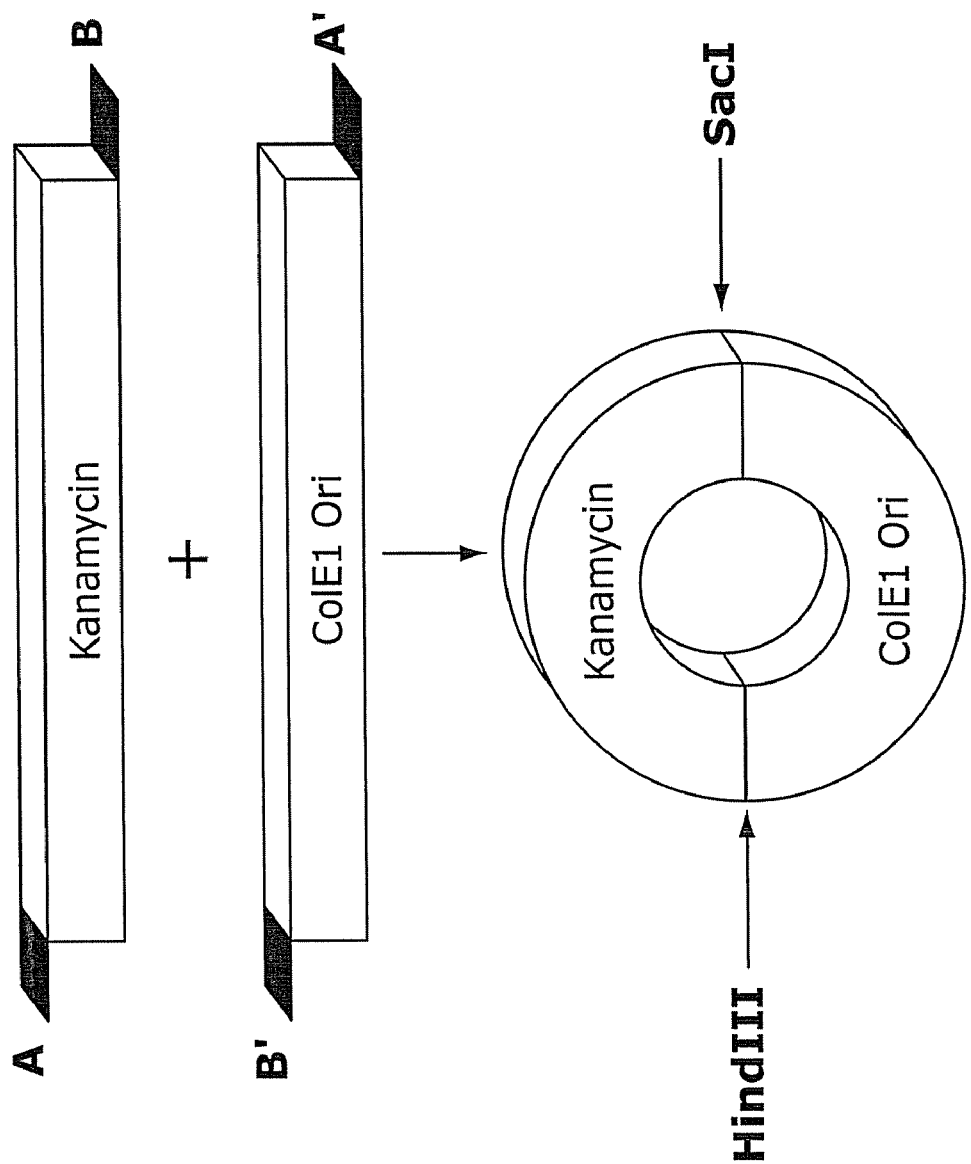
FIG. 12 shows a two-component modular vector system. This system was used to test various chimeric primers. Single-stranded tails generated by termination of polymerization are labeled A, A', B, and B'. Unique restriction sites were included in the overhangs to allow for easy indentification of recombinants and verification of junction sequence integrity.
Figure 15:
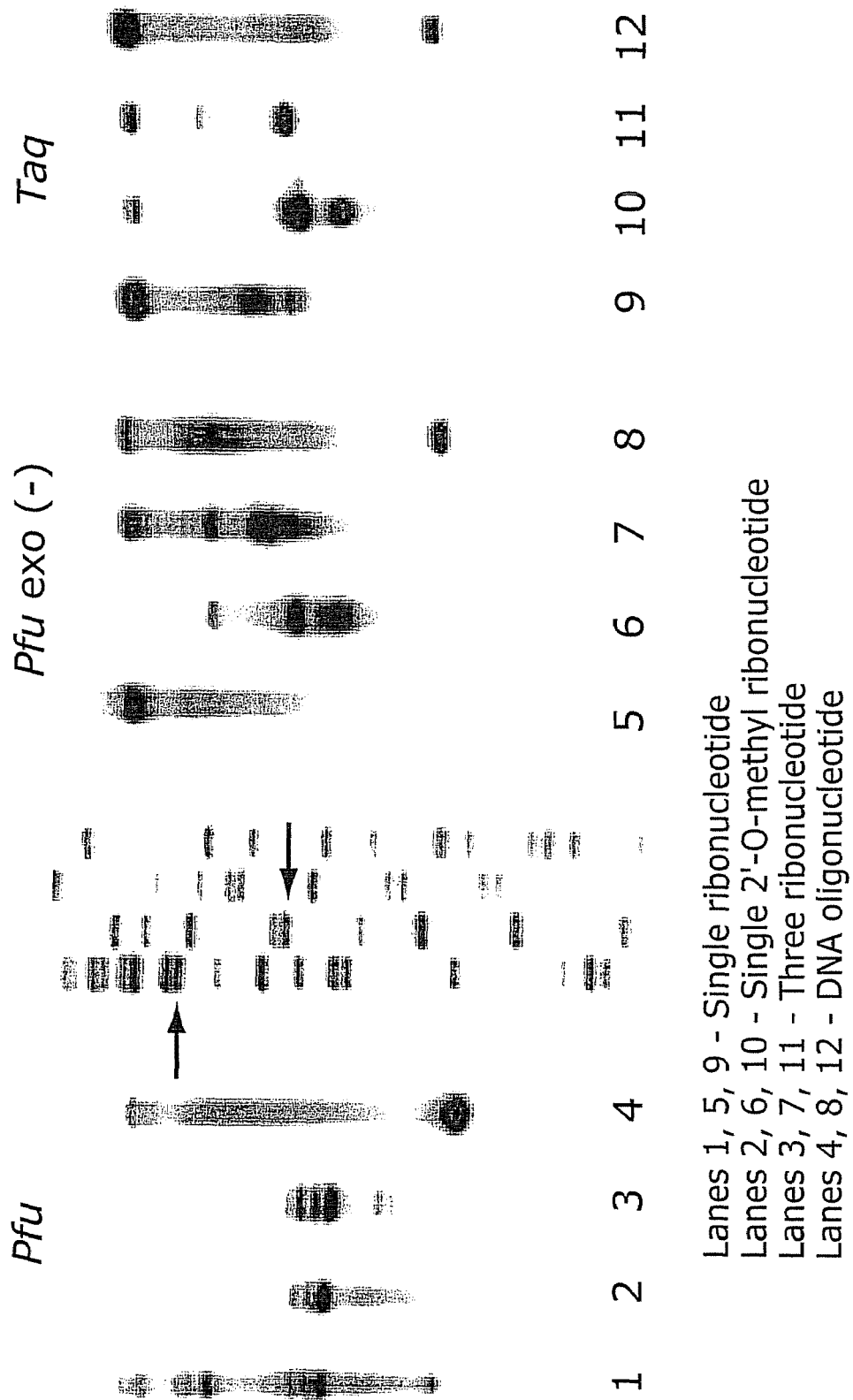
FIG. 15 depicts the termination of polymerization by single ribonucleotides (lanes 1, 5 and 9), single 2'-O-methyl nucleotides (lanes 2, 6, and 10), three ribonucleotides (lanes 3, 7 and 11), and DNA oligonucleotides (lanes 4, 8, and 12). PCR experiments were conducted with the following polymerases: Pfu (Lanes 1-4), Pfu exo-(lanes 5-8) and Taq (lanes 9-12). The same 32P-labeled primer was used as a PCR primer in each experiment. Four different unlabeled primers were used. The four primers were identical except for the inclusion of one or three ribonucleotides, or a single 2'-O-methyl nucleotide, at a particular position.
Figure 16:
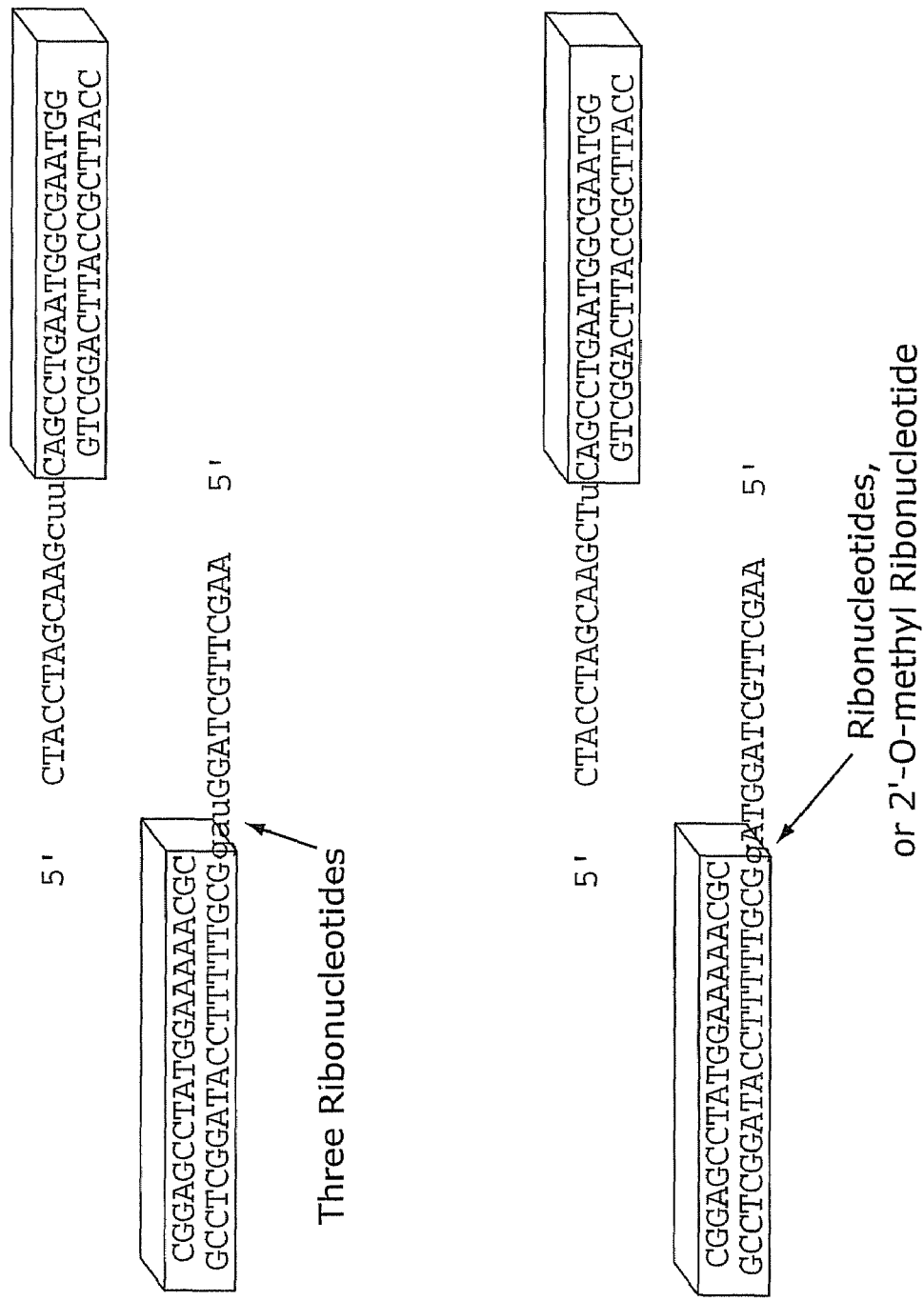
FIG. 16 shows a diagram of PCR products with tails generated by termination of polymerization by three ribonucleotides, or a single ribonucleotide or 2'-O-methyl ribonucleotide (ribonucleotides and 2'-O-methyl ribonucleotide are indicated by lower case residues)

Assembly of a Hybrid Vector/Insert Molecule Using ROC with Single Nucleotide Terminators The vector/insert hybrid molecule depicted in FIG. 10 was generated as follows. The ori-containing vector fragment was amplified from pET 19b (Novagen, Madison, Wis.) using primers (lower case letters indicate RNA residues; upper case letters indicate DNA residues) 5'OST (5'-CTGCTAAGT-GAGcucGACAGATCGCTGAGATAGGTGC; SEQ ID NO:5) and 1N3'Ori(s)(5'-AAGCTTGCTAAG-TAgGGCGTTTTTCCATAGGCTCCG; SEQ ID NO:6)

The vector fragment containing the Kanamycin resistance gene was amplified from pCR2.1 Topo (Invitrogen, Carlsbad, Calif.) using primers 1NT5'KAN (5' CTACCTAGCAAGC-TuCTATCTGGACAAGGGAAAACG; SEQ ID NO:7) and T7 3'KAN (5'CCCTATAGTGAGTCGTATTAaGGC-GAAAACTCTCAAGGATC; SEQ ID NO:8).

The insert fragment containing the luciferase gene was amplified from pGI II basic (Promega, Wis.) using primers tCS1 (5' TTAATACGACTCACTATAGG GATGGAAGACGCCAAAAACATA; SEQ ID NO: 9) and tCS8 (5'-GAGCTCACTTAGCA GTTACAATTTGGACTTTCCGCC; SEQ ID NO: 10).

Each 100 μl reaction contained 50 pM of each primer, 1× cloned Pfu Buffer (10 mM (NHy)$_2$SO$_4$, 20 mM Tris (pH 8.8), 2 mM Mg SO$_4$, 10 mM KCE, 0.1% Triten x-100 and 0.1 mg/me Bovine serum Albumin), 1 mM additional mg SO$_4$, 0.3 mM each dNTP, 5-10 ng template DNA and 1.25-1.85 units of both cloned Pfu and Pfu Turbo polymerases (strategies, La Jolla, Calif.). The Ori fragment was amplified in a reaction involving (1) one cycle of 95° for 3 min; 46-60° for 2 min; (2) 35 cycles of 95° for 30 sec; 48-60° for 30 sec; and 72° for 3 min; and (3) one cycle of 95° for 30 sec; 48-60° for 30 sec; and 72° for 8 min. The KAN and LUC fragments were amplified in similar reactions except that the 35 cycles contained a 4.5 min 72° step.

PCR products generated in these reactions were gel purified using the Qiaquick gel extraction kit (Qiagen, Valencia, Calif.). Approximately 80 ng of each fragment was combined in a 20 μl reaction volume. Two (2) μl 10×USB ligation Buffer (660 mM Tris-HCL (pH7.6), 66 mM MgCl$_4$, 100 mM DTT, 660 μM ATP) (USB, Cleveland, Ohio) was then added, to make a 1× reaction mix. The reaction was heated to 65° C. for 8 minutes, and then slow cooled for 20 minutes (to 35-40° C.) to allow the fragments to anneal. Samples were spun and allowed incubate another 15 minutes at room temperature.

The annealing reaction was precipitated by adding 100 μl of 100% ethanol, followed by a 15 minute incubation at −80° C., and a 70% and 100% wash. Electrocompetent DH5α cells were transformed using a Biorad *E. coli* pulser (Biorad, Hercules, Calif.). Five (5) μl of each annealing reaction was combined with 40 μl of Elexctromax DH5α-E cells (Life technologies, Rockville, Md.) Individual clones generated in this experiment were isolated, restriction mapped, and sequenced; all junctions were correct.

Those of ordinary skill in the art will appreciate that, as with Example 6, the ROC technique described in this Example utilizes primers containing internal ribonucleotide residues (in one case, 3 residues were used; in other cases only one) flanked by DNA residues. The overhangs created in these ROC PCR reactions, therefore, have only a single "ribo" residue; other overhang residues are DNA. In separate experiments, we have demonstrated that any individual ribonucleotide (i.e., rA, rG, rU, or rC) can act effectively to block extension of a complimentary strand by an appropriate DNA polymerase, so that overhangs are created (see, for example, Example 6). We have also showed that single 2'-O-methyl residues are similarly effective (see Example 10). Primers containing 2'-O-methyl residues can often be synthesized more easily (e.g., due to higher coupling efficiencies) than those containing ribonucleotides, and will generally be more stable, so that they are preferred for many applications.

Example 8

Streamlined Cloning

Inventive modular vector fragments may be prepared, annealed together, and transformed into host cells, without enzymatic ligation. For example, we assembled a two-fragment vector, by preparing one fragment (KAN) containing the kanamycin resistance gene, and one fragment (Ori) containing an origin of replication.

Specifically, two 100 µl PCR reactions were performed to amplify each of the two components of the vector. Each reaction contained 50 pM of each primer, 1× Cloned Pfu Buffer (10 mM (NH$_4$)$_2$SO$_4$, 20 mM Tris (pH 8.8), 2 mM MgSO$_4$, 10 mM KCl, 0.1% Triton X-100 and 0.1 mg/ml bovine serum albumin), 1 mM additional MgSO$_4$, 0.3 mM of each dNTP, 5-10 ng of plasmid template and 1.25-1.85 units of both cloned Pfu and Pfu Turbo polymerases (Stratagene, La Jolla, Calif.).

The following chimeric RNA/DNA primers were purchased from Oligo's Etc. (Willsonville, Oreg.): (ribonucleotides are in lower case)

```
                                        (SEQ ID NO:11)
1NT 5'KAN-CTACCTAGCAAGCTuCTATCTGGACAAGGGAAAACG (SEQ ID NO:12)
1NT 3'KAN-GAGCTCACTTAGCAAGGCGAAAACTCTCAAGGA (SEQ ID NO:13)
1NT5'Ori-TTGCTAAGTGAGCTcGACAGATCGCTGAGATAGGTGC (SEQ ID NO:14)
1NT3'Ori(s)-AAGCTTGCTAAGTAgGGCGTTTTTCCATAGGCTCCG.
```

Primers 1NT 5'KAN and 1NT 3'KAN were used to amplify the Kan fragment from pCR 2.1 Topo (Invitrogen, Carlsbad, Calif.). Primers 1NT5'Ori and 1NT3'Ori(s) were used to amplify the Ori fragment from pET 19b (Novagen, Madison, Wis.). The following cycles were performed: one cycle of 95°, 3', 48-60°, 2', 72°, 8'; followed by 35 cycles of 95°, 30 sec, 48-60°, 30 sec, 72°, 3' for Ori fragment, 4.5' for Kan and Luc fragments. A final cycle with an 8' 72° step was performed in all cases.

Approximately 80 ng of each fragment (5 µl each) produced in the PCR reactions was combined and mixed. 5 µl of this reaction was then transformed into 100 µl of chemically competent DH5α cells without a DNA purification step or an annealing step. Positive clones were isolated and mapped; sequence junctions appear to be correct.

Example 9

Varying the Length of the Overhang

Ligation dependent experiments were performed in which the length of the overhang was shortened to six, three and one nucleotide(s). These experiments used chimeric primers consisting of a variable number of 5' DNA nucleotides followed by a single ribonucleotide and a stretch of template binding DNA nucleotides. Thus, the overhangs included five, two or zero DNA nucleotides, respectively. All three of these primer configurations produce accurately ligated vectors, however, the yield of colonies was approximately 170-fold lower when a single ribonucleotide overhang was used (850,000 colonies per µg vs. 5,000 colonies per µg). DNA sequence analysis revealed one case of a duplicated junction, apparently created by blunt end ligation of PCR products, suggesting that the terminator nucleotide was being read through at some frequency. Blunt ended fragments had not been detected in previous experiments, most likely due to the ligation-independent procedure that was used.

Example 10

Cloning with 2'-O-Methyl Terminator Primers

Modules, DNA templates, and primers (Table 1). Three primers are shown for each vector module. The 2'-O-methyl residues are underlined. When plasmids were assembled from two components, the first two primers in each set were used in PCR. When plasmids were assembled from three components, the first and third primers in each set were used in PCR.

PCR. Each 100 µl reaction contained 50 pMol of each primer, 1×Pfu Buffer (10 mM (NH$_4$)$_2$SO$_4$, 20 mM Tris (pH8.8), 2 mM MgSO$_4$, 10 mM KCl, 0.1% Triton X-100 and 1 mg/ml bovine serum albumin), 1 mM additional MgSO$_4$, 0.3 mM of each dNTP, 5-10 ng of plasmid template and 1.25-1.85 units each of cloned Pfu and Pfu Turbo polymerases (Stratagene, La Jolla, Calif.). Chimeric RNA/DNA primers were purchased from Oligo's Etc. (Willsonville, Oreg.). A typical step program for PCR was as follows: one cycle of 95°, 3'; 52°, 2' followed by 30 cycles of 95°, 30 sec; 52°, 30 sec; 72°, 2'.

Annealing Reaction. When annealing reactions were performed, PCR products were gel purified from a 1% agarose gel, using the Qiaquick gel extraction kit (Qiagen, Valencia, Calif.). Approximately 80 ng of each fragment were combined in a 20 µl reaction that included 2 µl of 10×USB ligation Buffer (660 mM Tris-HCL (pH7.6), 66 mM MgCl$_2$, 100 mM DTT, 660 µM ATP) (USB, Cleveland, Ohio) was added make a 1× annealing mix. The reaction was heated to 65° C. for 8 minutes, then cooled for 20 minutes to approximately 35-40° C. Samples were centrifuged briefly and incubated another 15 minutes at room temperature.

Transformation. Annealing reactions, when performed, were precipitated by adding 100 µl of 100% ethanol, followed by a 15 minute incubation at −80° C., centrifugation, and 70% and 100% ethanol washes. Electrocompetent DH5α cells were transformed using a Biorad E. coli pulser (Biorad, Hercules, Calif.); 5 µl of each annealing reaction were combined with 40 µl of Electromax DH5α-E cells (Life Technologies, Rockville, Md.)

Simplified PCR cloning. For simplified cloning experiments, we combined 5 µl of the Kan PCR reaction with 5 µl of the Ori PCR reaction and added the sample to 100 µl of chemically competent E. coli cells. The mixture was incubated on ice for 15' followed by a 45 second heat shock at 42° C. Cells were incubated on ice for another 2' before 800 µl of LB media was added. Cells were incubated with shaking for 45' at 37° C. before plating.

Labeling of primers. One nMol of the a DNA primer called 5'Amp S/PE (5'-TGAGAGTGCACCATATGCG [SEQ ID NO: 45]) was combined with 5 µl of γ-$^{32}$P labeled ATP (3000 Ci/mMol), 5 µl of 10×PNK buffer (330 mM Tris-acetate (pH 7.8), 660 mM potassium acetate, 100 mM magnesium acetate, and 5 mM DTT), 2 µl (20 units) T4 polynucleotide kinase (Epicentre, Madison, Wis.), and H$_2$O to 5 µl. Reactions were incubated for 30' at 37° C.

Sequence ladder. A DNA sequencing reaction was performed using the Sequenase 2.0 DNA sequencing kit (USB, Cleveland, Ohio) with the Amp/ColE1 vector as a template. Reactions contained 0.5 µl of α-$^{32}$P labeled ATP (800 Ci/mMol), 25 pMol primer and 1 µg DNA.

PCR reactions. Each 100 µl Pfu PCR reaction contained 50 pMol of each primer, 1× Cloned Pfu Buffer (10 mM (NH$_4$)$_2$SO$_4$, 20 mM Tris (pH 8.8), 2 mM MgSO$_4$, 10 mM KCl, 0.1% Triton X-100 and 0.1 mg/ml bovine serum albumin), 1 mM additional MgSO$_4$, 0.3 mM of each dNTP, 5-10 ng of plasmid template and 1.25 units of both cloned Pfu and Pfu Turbo polymerases (Stratagene, La Jolla, Calif.). Pfu exo (−) reactions contained 2.5 units of Pfu exo (−) polymerase (Stratagene, La Jolla, Calif.); Each 100 µl Taq PCR reaction contained 50 pMol of each primer, 1×Taq buffer (10× Reaction Buffer without MgCl$_2$: 500 mM KCl, 100 mM Tris-HCl (pH 9.0 at 25° C.) and 1.0% Triton® X-100), 1 mM MgCl$_2$, 0.1 mM of each dNTP, 5 units Taq polymerase in storage buffer A (Promega, Madison, Wis.).

PCR Cycling. One cycle of 95°, 3'; 52°, 2'; 72°, 15 seconds, followed by 30 cycles of 95°, 30 sec; 55°, 30 sec; 72°, 15 seconds. Chimeric RNA/DNA primers were purchased from Oligo's Etc.(Willsonville, Oreg.).

Using the techniques set out above, we tested whether primers that harbored a single 2'-O-methyl nucleotide rather than a single ribonucleotide could be used as terminator primers. These chimeric 2'-O-methyl primers demonstrated greatly improved cloning efficiency. We obtained 500,000 colonies per µg of DNA. Thus, cloning with primers containing a single 2'-O-methyl nucleotides is 25-fold more efficient than cloning with primers that harbor single ribonucleotides. We tested each of the four possible 2'-O-methyl nucleotides and found that each of the four nucleotides functions to generate an overhang for terminator cloning.

In order to confirm the presence of the single stranded overhangs, and compare termination efficiencies with different types of chimenic primers and polymerases, we designed an experiment that used radiolabeled primers in terminator PCR (t-PCR) reactions. A $^{32}$P labeled DNA reverse primer and a chimenic forward primer were used in a PCR reaction to generate a 100 base pair (bp) product. These reactions were denatured and resolved on an 8% polyacrylamide gel (FIG. 13B). If the polymerase terminates at the terminator nucleotide(s) an 85 nucleotide labeled product is expected. Full read-through to the end of the chimeric primer would generate a 100 nucleotide labeled product. The sequences of all chimeric primers were identical, and were varied only with respect to the type of nucleotide(s) comprising the terminator positions (i.e., ribo, deoxy, 2'-O-methyl). The same $^{32}$P labeled DNA reverse primer was used for all experiments.

The following primers were tested: a DNA primer, an RNA/DNA primer with ribonucleotides at positions 13, 14, 15, an RNA/DNA primer with a single ribonucleotide at position 15, and a primer with a single 2'-O-methyl nucleotide at position 15. Pfu, Pfu(exo−), and Taq polymerases were tested.

The radiolabeled PCR experiments confirmed that there is a stop or pause induced by the terminator residues. PCR reactions using Pfu polymerase demonstrated termination with all versions of the terminator primers as expected. However, there was significant read through with the single ribonucleotide primer (FIG. 13B, lane 1). The experiment with Pfu(exo−) demonstrates that the 3'-5' exonuclease activity of Pfu is important for termination since Pfu(exo−), which lacks the 3'-5' exonuclease activity, reads through the terminator with high efficiently (Lanes 5-7). PCR reactions using Taq polymerase showed little termination by RNA nucleotides, but did appear to be strongly stopped by the 2'-O-methyl residue.

We expected termination to occur one nucleotide prior to the terminator residue. Although Pfu terminated at that position, termination also occurred two nucleotides or three nucleotides prior to the expected position. Thus, termination generated a population of molecules, with tails of 15, 16 or 17 nucleotides.

An unexpected early termination was observed adjacent to the template region of both the DNA control primer and the single ribonucleotide chimeric primer (FIG. 13B, asterisk). This stop was not seen in the three ribonucleotide or 2'-O-methyl t-PCR reactions. The mechanism of this unexpected termination is unknown.

We developed the t-PCR cloning method described above as a tool for creating useful biological diversity by linking together modular DNA elements in a ligation independent manner. We tested this approach by using the method to clone genes while simultaneously assembling the vectors into which the genes were cloned.

The modular vector system works in the following way. Vector elements (i.e., drug resistance genes, replication origins, or insert genes) are amplified with Pfu polymerase using 2'-O-methyl terminator primers. The overhangs on the amplified vector elements (modules) follow a specific set of rules that allow similar functional modules to be interchanged in a standardized orientation. Modules can be inserted or substituted into existing vectors or can be combined to construct new vectors.

Combining drug resistance and origin of replication modules with insert modules produces cloned genes in customized vectors (FIG. 14). We constructed a set of vectors using two possible origins of replication, three possible drug resistance genes, and two different marker genes. These fragments were combined in all possible combinations to generate a total of 18 distinct plasmids.

Six vectors were produced in two molecule reactions that contained no insert (FIG. 14A) The GFP and LacZ containing vectors were assembled in three molecule reactions (FIG. 14B), but were also assembled using two molecule reactions in order to compare cloning efficiencies between two and three molecule cloning. We find that two molecule assembly experiments are more efficient than three molecule assembly experiments. For example, cloning of GFP or LacZ via a two molecule experiment is approximately 6-fold more efficient than cloning of the same gene via a three molecule experiment (1400 colonies per µg vs. 240 colonies per µg). Unexpectedly, however we find that the efficiency of two molecule assembly varies significantly depending on the design of the experiment. The two molecule assembly experiments that combined a resistance gene with an origin of replication (FIG. 14A), were typically 450-fold more efficient than the experiments that combined a marker gene (i.e., LacZ or GFP) with an entire amplified plasmid. The reason for this difference in efficiency remains to be determined.

We have successfully completed thirty modular assembly experiments. Twenty-five of the plasmids were produced on the first attempt. All recombinants were confirmed by restriction mapping. Approximately 80% of the plasmids that were mapped (90/116) exhibited the expected recombinant restriction map. Fifteen ligation junctions were sequenced, and fourteen junctions were free of point mutations. We conclude that t-PCR cloning provides a rapid and accurate method for gene cloning and modular vector assembly.

Other Embodiments

Those of ordinary skill in the art will appreciate that the foregoing represents certain preferred embodiments of the invention, but is not intended to limit the spirit or scope of the following claims.

The invention claimed is:

1. A method of generating a double-stranded DNA molecule, the method comprising steps of:
providing a template nucleic acid molecule;
contacting the template nucleic acid molecule with a first primer that hybridizes thereto, the first primer including at least one termination residue consisting of a 2'-O-methyl residue;

extending the first primer so that a nucleic acid strand complementary to that with which the first primer hybridizes is generated;

contacting the complementary nucleic acid strand with a second primer that hybridizes thereto;

extending the second primer with a DNA polymerase that does not copy the 2'-O-methyl residue, so that the extension reaction produces a product molecule containing a first overhang;

providing a second double-stranded DNA molecule containing a second overhang at least partly complementary to the first overhang; and combining the second double-stranded DNA molecule with the generated double-stranded DNA molecule under conditions that allow hybridization of the first and second overhangs.

2. The method of claim 1, wherein the second double-stranded DNA molecule contains an overhang that includes a portion that is not complementary to the first overhang.

3. The method of claim 1, further comprising the step of ligating the second double-stranded DNA molecule and the generated double-stranded DNA molecule to each other.

4. The method of claim 3, wherein the step of ligating occurs in vivo.

5. The method of claim 3, wherein the step of ligating occurs in vitro.

6. A method of generating a nucleic acid molecule, the method comprising steps of:

generating a plurality of precursor nucleic acid molecules, each of which is generated by providing a template nucleic acid molecule;

contacting the template nucleic acid molecule with a first primer that hybridizes thereto the first primer including at least one termination residue consisting of a 2'-O-methyl residue;

extending the first primer so that a nucleic acid strand complementary to that with which the first primer hybridizes is generated;

contacting the complementary nucleic acid strand with a second primer that hybridizes thereto;

extending the second primer with a DNA polymerase that does not copy the 2'-O-methyl residue, so that the extension reaction produces a product molecule containing a first overhang;

wherein the primers used to generate each precursor nucleic acid molecule are selected so that each overhang is complementary, at least in part, to an overhang belonging to another of the precursor nucleic acid molecules; and combining the plurality of precursor nucleic acid molecules with one another under conditions that allow hybridization of the complementary overhangs, so that a nucleic acid molecule is generated.

7. A method of generating a plurality of nucleic acid molecules, the method comprising steps of:

generating a first plurality of precursor nucleic acid molecules, each of which is by providing a template nucleic acid molecule;

contacting the template nucleic acid molecule with a first primer that hybridizes thereto, the first primer including at least one termination residue consisting of a 2'-O-methyl residue;

extending the first primer so that a nucleic acid strand complementary to that with which the first primer hybridizes is generated;

contacting the complementary nucleic acid strand with a second primer that hybridizes thereto;

extending the second primer with a DNA polymerase that does not copy the 2'-O-methyl residue, so that the extension reaction produces a product molecule containing a first overhang;

wherein the primers used to generate each precursor nucleic acid molecule are selected so that each overhang is complementary, at least in part, to an overhang belonging to another of the precursor nucleic acid molecules; and combining various precursor nucleic acid molecules from the first plurality of precursor nucleic acid molecules with one another, under conditions that allow hybridization of the complementary overhangs, so that a plurality of nucleic acid molecules is generated.

8. A method of generating a nucleic acid molecule, the method comprising steps of:

generating a plurality of precursor nucleic acid molecules, each of which is generated by providing a template nucleic acid molecule;

contacting the template nucleic acid molecule with a first primer that hybridizes thereto, the first primer including at least one termination residue consisting of a 2'-O-methyl residue,;

extending the first primer so that a nucleic acid strand complementary to that with which the first primer hybridizes is generated;

contacting the complementary nucleic acid strand with a second primer that hybridizes thereto;

extending the second primer with a DNA polymerase that does not copy the 2'-O-methyl residue, so that the extension reaction produces a product molecule containing a first overhang;

wherein the primers are selected so that each precursor nucleic acid molecule comprises an overhang that has a sequence distinct from that of the overhangs belonging to any of the other precursor nucleic acid molecules; and combining the plurality of precursor nucleic acid molecules with one another under conditions that allow hybridization of the complementary overhangs, so that a nucleic acid molecule is generated.

9. A method of generating a plurality of nucleic acid molecules, the method comprising the steps of:

generating a plurality of precursor nucleic acid molecules, each of which is generated by providing a template nucleic acid molecule;

contacting the template nucleic acid molecule with a first primer that hybridizes thereto, the first primer including at least one termination residue consisting of a 2'-O-methyl residue;

extending the first primer so that a nucleic acid strand complementary to that with which the first primer hybridizes is generated;

contacting the complementary nucleic acid strand with a second primer that hybridizes thereto;

extending the second primer with a DNA polymerase that does not copy the 2'-O-methyl residue, so that the extension reaction produces a product molecule containing a first overhang;

wherein the primers are selected so that each precursor nucleic acid molecule comprises an overhang that has a sequence distinct from that of the overhangs belonging to any of the other precursor nucleic acid molecules; and combining the plurality of precursor nucleic acid molecules with one another, under conditions that allow hybridization of the complementary overhangs, so that a plurality of nucleic acid molecules is generated.

10. The method of claim 6 or 8, further comprising a step of ligating the plurality of nucleic acid molecules to one another.

11. The method of claim 7 or 9, further comprising a step of ligating the first plurality of nucleic acid molecules to one another, thereby generating a second plurality of nucleic acid molecules.

12. The method of claim 10, wherein the step of ligating occurs in vivo.

13. The method of claim 10, wherein the step of ligating occurs in vitro.

14. The method of claim 11, wherein the step of ligating occurs in vivo.

15. The method of claim 11, wherein the step of ligating occurs in vitro.

* * * * *